US011944310B2

(12) United States Patent
Shelton, IV et al.

(10) Patent No.: US 11,944,310 B2
(45) Date of Patent: Apr. 2, 2024

(54) NON-CIRCULAR END EFFECTOR FEATURES FOR SURGICAL STAPLER

(71) Applicant: Cilag GmbH International, Zug (CH)

(72) Inventors: Frederick E. Shelton, IV, Hillsboro, OH (US); Gregory J. Bakos, Mason, OH (US); Shannon L. Jones, Cincinnati, OH (US); Jason L. Harris, Lebanon, OH (US)

(73) Assignee: Cilag GmbH International, Zug (CH)

( * ) Notice: Subject to any disclaimer, the term of this patent is extended or adjusted under 35 U.S.C. 154(b) by 9 days.

(21) Appl. No.: 17/401,430

(22) Filed: Aug. 13, 2021

(65) Prior Publication Data

US 2023/0045940 A1 Feb. 16, 2023

(51) Int. Cl.
*A61B 17/115* (2006.01)
*A61B 17/072* (2006.01)
*A61B 17/11* (2006.01)

(52) U.S. Cl.
CPC . *A61B 17/1155* (2013.01); *A61B 2017/07228* (2013.01); *A61B 2017/07264* (2013.01); *A61B 2017/07285* (2013.01); *A61B 17/1114* (2013.01); *A61B 2017/1132* (2013.01)

(58) Field of Classification Search
CPC ...... A61B 17/1155; A61B 2017/07257; A61B 2017/07271; A61B 2017/07264; A61B 2017/07285
See application file for complete search history.

(56) References Cited

U.S. PATENT DOCUMENTS

| 2,277,931 | A | | 3/1942 | Moe |
| 4,047,654 | A | * | 9/1977 | Alvarado ............. A61B 17/115 227/19 |
| 4,407,286 | A | | 10/1983 | Noiles et al. |

(Continued)

FOREIGN PATENT DOCUMENTS

| EP | 1875870 A1 | 1/2008 |
| EP | 2157918 | 3/2010 |

(Continued)

OTHER PUBLICATIONS

U.S. Appl. No. 17/401,391, entitled, "Methods of Forming an Anastomosis Between Organs with an Expandable Pattern," filed Aug. 13, 2021.

(Continued)

*Primary Examiner* — Andrew M Tecco
(74) *Attorney, Agent, or Firm* — Frost Brown Todd LLP

(57) ABSTRACT

A surgical instrument including a stapling assembly and an anvil configured to selectively couple with the stapling assembly to compress tissue and form staples in the tissue. The stapling assembly includes a housing extending distally along a central axis, a deck member having a plurality of staple openings configured to receive a plurality of staples, and a knife member at least partially disposed within the housing. The deck member includes an exterior perimeter having a first shape and an interior perimeter enclosed by the exterior perimeter and having a second shape different than the first shape. The knife member includes a distal end having a cutting edge that defines an edge plane that intersects the central axis. The cutting edge has a non-circular shape in the edge plane.

17 Claims, 18 Drawing Sheets

(56) References Cited

U.S. PATENT DOCUMENTS

| | | | |
|---|---|---|---|
| 4,505,273 A | 3/1985 | Braun et al. |
| 4,669,647 A | 6/1987 | Storace |
| 4,848,328 A | 7/1989 | Laboureau et al. |
| 4,874,122 A | 10/1989 | Froelich et al. |
| 4,899,745 A | 2/1990 | Laboureau et al. |
| 5,292,053 A | 3/1994 | Bilotti et al. |
| 5,309,927 A | 5/1994 | Welch |
| 5,333,773 A | 8/1994 | Main et al. |
| 5,342,396 A | 8/1994 | Cook |
| 5,350,104 A | 9/1994 | Main et al. |
| 5,425,489 A | 6/1995 | Shichman et al. |
| 5,533,661 A | 7/1996 | Main et al. |
| 5,725,554 A | 3/1998 | Simon et al. |
| 5,732,872 A | 3/1998 | Bolduc et al. |
| 5,993,468 A | 11/1999 | Rygaard |
| 6,352,541 B1 | 3/2002 | Kienzle et al. |
| 6,425,903 B1 | 7/2002 | Voegele |
| 6,616,686 B2 | 9/2003 | Coleman et al. |
| 6,629,630 B2 | 10/2003 | Adams |
| 6,767,356 B2 | 7/2004 | Kanner et al. |
| 6,769,590 B2 | 8/2004 | Vresh et al. |
| 6,915,937 B2 | 7/2005 | Lat et al. |
| 6,978,922 B2 | 11/2005 | Bilotti et al. |
| 7,056,330 B2 | 6/2006 | Gayton |
| 7,422,138 B2 | 9/2008 | Bilotti et al. |
| 7,722,643 B2 | 5/2010 | Schaller et al. |
| 7,824,426 B2 | 11/2010 | Racenet et al. |
| 7,934,630 B2 | 5/2011 | Shelton, IV et al. |
| 8,062,330 B2 | 11/2011 | Prommersberger et al. |
| 8,143,870 B2 | 3/2012 | Ng et al. |
| 8,231,042 B2 | 7/2012 | Hessler et al. |
| 8,267,301 B2 | 9/2012 | Milliman et al. |
| 8,328,063 B2 | 12/2012 | Milliman et al. |
| 8,393,516 B2 | 3/2013 | Kostrzewski |
| 8,413,870 B2 | 4/2013 | Pastorelli et al. |
| 8,613,384 B2 | 12/2013 | Pastorelli et al. |
| 8,684,254 B2 | 4/2014 | Kostrzewski |
| 8,789,738 B2 | 7/2014 | Knodel et al. |
| 8,801,732 B2 | 8/2014 | Harris et al. |
| 8,910,847 B2 | 12/2014 | Nalagatla et al. |
| 8,978,954 B2 | 3/2015 | Shelton, IV et al. |
| 9,016,541 B2 | 4/2015 | Viola et al. |
| 9,192,387 B1 | 11/2015 | Holsten et al. |
| 9,265,500 B2 | 2/2016 | Sorrentino et al. |
| 9,402,628 B2 | 8/2016 | Beardsley |
| 9,629,624 B2 | 4/2017 | Hessler et al. |
| 9,713,469 B2 | 7/2017 | Leimbach et al. |
| 9,730,694 B2 | 8/2017 | Scirica et al. |
| 9,782,171 B2 | 10/2017 | Viola |
| 9,848,874 B2 | 12/2017 | Kostrzewski |
| 9,907,552 B2 | 3/2018 | Measamer et al. |
| 9,936,949 B2 | 4/2018 | Measamer et al. |
| 9,987,013 B2 | 6/2018 | Eckert et al. |
| 10,080,565 B2 | 9/2018 | Pastorelli et al. |
| 10,105,134 B2 | 10/2018 | Biedermann et al. |
| 10,130,359 B2 | 11/2018 | Hess et al. |
| 10,136,888 B2 | 11/2018 | Chen et al. |
| 10,166,026 B2 | 1/2019 | Shelton, IV et al. |
| 10,285,705 B2 | 5/2019 | Shelton, IV et al. |
| 10,327,776 B2 | 6/2019 | Harris et al. |
| 10,433,849 B2 | 10/2019 | Shelton, IV et al. |
| 10,603,041 B2 | 3/2020 | Miller et al. |
| 10,611,060 B2 | 4/2020 | Stopek et al. |
| 10,639,040 B2 | 5/2020 | Penna et al. |
| 10,709,452 B2 | 7/2020 | DiNardo et al. |
| 10,856,867 B2 | 12/2020 | Shelton, IV et al. |
| 10,869,663 B2 | 12/2020 | Shelton, IV et al. |
| 10,925,607 B2 | 2/2021 | Penna et al. |
| 11,147,559 B2 | 10/2021 | Wise et al. |
| 11,241,232 B2 | 2/2022 | Guerrera |
| 11,284,890 B2 | 3/2022 | Nalagatla et al. |
| 11,291,450 B2 | 4/2022 | Nalagatla et al. |
| 11,523,821 B2 | 12/2022 | Harris et al. |
| 2003/0009193 A1 | 1/2003 | Corsaro |
| 2004/0073237 A1 | 4/2004 | Leinsing |
| 2006/0291981 A1 | 12/2006 | Viola et al. |
| 2008/0082126 A1 | 4/2008 | Murray et al. |
| 2008/0294179 A1* | 11/2008 | Balbierz ............... A61B 17/10 |
| | | | 606/151 |
| 2009/0188964 A1 | 7/2009 | Orlov |
| 2010/0191262 A1 | 7/2010 | Harris et al. |
| 2011/0011916 A1* | 1/2011 | Levine ............... A61B 17/115 |
| | | | 227/179.1 |
| 2011/0017800 A1* | 1/2011 | Viola ................. A61B 17/115 |
| | | | 227/175.1 |
| 2012/0080498 A1 | 4/2012 | Shelton, IV et al. |
| 2012/0193395 A1 | 8/2012 | Pastorelli et al. |
| 2012/0325893 A1* | 12/2012 | Pastorelli ............ A61B 17/115 |
| | | | 227/177.1 |
| 2014/0027493 A1 | 1/2014 | Jankowski |
| 2014/0158747 A1 | 6/2014 | Measamer et al. |
| 2015/0083772 A1 | 3/2015 | Miller et al. |
| 2016/0278768 A1 | 9/2016 | Johnson et al. |
| 2017/0119397 A1 | 5/2017 | Harris et al. |
| 2017/0333064 A1* | 11/2017 | Ebner ................ A61B 17/285 |
| 2018/0132849 A1 | 5/2018 | Miller et al. |
| 2018/0235635 A1 | 8/2018 | Rekstad et al. |
| 2018/0242974 A1 | 8/2018 | Guerrera et al. |
| 2018/0325508 A1 | 11/2018 | Aronhalt et al. |
| 2020/0038017 A1 | 2/2020 | Hess et al. |
| 2020/0054339 A1 | 2/2020 | Scirica et al. |
| 2020/0229814 A1 | 7/2020 | Amariglio et al. |
| 2023/0049242 A1 | 2/2023 | Jones et al. |
| 2023/0102965 A1 | 3/2023 | Wise et al. |

FOREIGN PATENT DOCUMENTS

| | | |
|---|---|---|
| EP | 2649949 A1 | 10/2013 |
| EP | 3225176 A1 | 10/2017 |
| EP | 3225179 A1 | 10/2017 |
| EP | 3245958 A1 | 11/2017 |
| EP | 3130292 B1 | 8/2018 |
| EP | 3173030 B1 | 10/2019 |
| WO | WO 2001/054594 A1 | 8/2001 |
| WO | WO 2002/009595 A1 | 2/2002 |
| WO | WO 2005/115254 A2 | 12/2005 |
| WO | WO 2008/141288 A1 | 11/2008 |
| WO | 3643252 A1 | 4/2020 |
| WO | WO 2020/249487 A1 | 12/2020 |

OTHER PUBLICATIONS

U.S. Appl. No. 17/401,428, entitled, "Staple Forming Features for Circular Surgical Stapler," filed Aug. 13, 2021.
U.S. Appl. No. 17/401,439, entitled, "Circular Surgical Stapler End Effector Having Staple Line Alignment Feature," filed Aug. 13, 2021.
U.S. Appl. No. 17/401,444, entitled, "Circular Surgical Stapler for Forming Pattern of Non-Tangential Staples," filed Aug. 13, 2021.
U.S. Appl. No. 17/401,451, entitled, "Circular Surgical Stapler Having Staples with Expandable Crowns," filed Aug. 13, 2021.
U.S. Appl. No. 17/401,460, entitled, "Circular Surgical Stapler for Forming Cross-Pattern of Staples," filed Aug. 13, 2021.
U.S. Appl. No. 17/401,391.
U.S. Appl. No. 17/401,428.
U.S. Appl. No. 17/401,439.
U.S. Appl. No. 17/401,451.
U.S. Appl. No. 17/489,965.
U.S. Pat. No. 11,653,926.
U.S. Pat. No. 11,666,339.
International Search Report and Written Opinion dated Nov. 14, 2022 for Application No. PCT/IB2022/057444, 12 pgs.
International Search Report and Written Opinion dated Jan. 27, 2023 for Application No. PCT/IB2022/057446, 19 pgs.
International Search Report and Written Opinion dated Nov. 23, 2022 for Application No. PCT/IB2022/057449, 15 pgs.
International Search Report and Written Opinion dated Jan. 25, 2023 for Application No. PCT/IB2022/057442, 20 pgs.
International Search Report and Written Opinion dated Nov. 14, 2022 for Application No. PCT/IB2022/057443, 12 pgs.

(56) References Cited

OTHER PUBLICATIONS

International Search Report and Written Opinion dated Nov. 24, 2022 for Application No. PCT/IB2022/057451, 13 pgs.

\* cited by examiner

US 11,944,310 B2

NON-CIRCULAR END EFFECTOR FEATURES FOR SURGICAL STAPLER

BACKGROUND

A circular surgical stapler may be used to form an anastomosis between two organ portions of a patient's digestive tract. Examples of circular surgical staplers are described in U.S. Pat. No. 5,292,053, entitled "Surgical Anastomosis Stapling Instrument," issued Mar. 8, 1994; U.S. Pat. No. 5,333,773, entitled "Surgical Anastomosis Stapling Instrument," issued Aug. 2, 1994; U.S. Pat. No. 5,350,104, entitled "Surgical Anastomosis Stapling Instrument," issued Sep. 27, 1994; and U.S. Pat. No. 5,533,661, entitled "Surgical Anastomosis Stapling Instrument," issued Jul. 9, 1996; and U.S. Pat. No. 8,910,847, entitled "Low Cost Anvil Assembly for a Circular Stapler," issued Dec. 16, 2014. The disclosure of each of the above-cited U.S. Patents is incorporated by reference herein.

Some circular staplers may include a motorized actuation mechanism. Examples of circular staplers with motorized actuation mechanisms are described in U.S. Pub. No. 2015/0083772, entitled "Surgical Stapler with Rotary Cam Drive and Return," published Mar. 26, 2015, now abandoned; U.S. Pat. No. 9,936,949, entitled "Surgical Stapling Instrument with Drive Assembly Having Toggle Features," issued Apr. 10, 2018; U.S. Pat. No. 9,907,552, entitled "Control Features for Motorized Surgical Stapling Instrument," issued Mar. 6, 2018; U.S. Pat. No. 9,713,469, entitled "Surgical Stapler with Rotary Cam Drive," issued Jul. 25, 2017; U.S. Pub. No. 2018/0132849, entitled "Staple Forming Pocket Configurations for Circular Surgical Stapler Anvil," published May 17, 2018, now abandoned; and U.S. Pat. No. 10,709,452, entitled "Methods and Systems for Performing Circular Stapling," issued Jul. 14, 2020. The disclosure of each of the above-cited U.S. Patent Publications and U.S. Patents is incorporated by reference herein.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
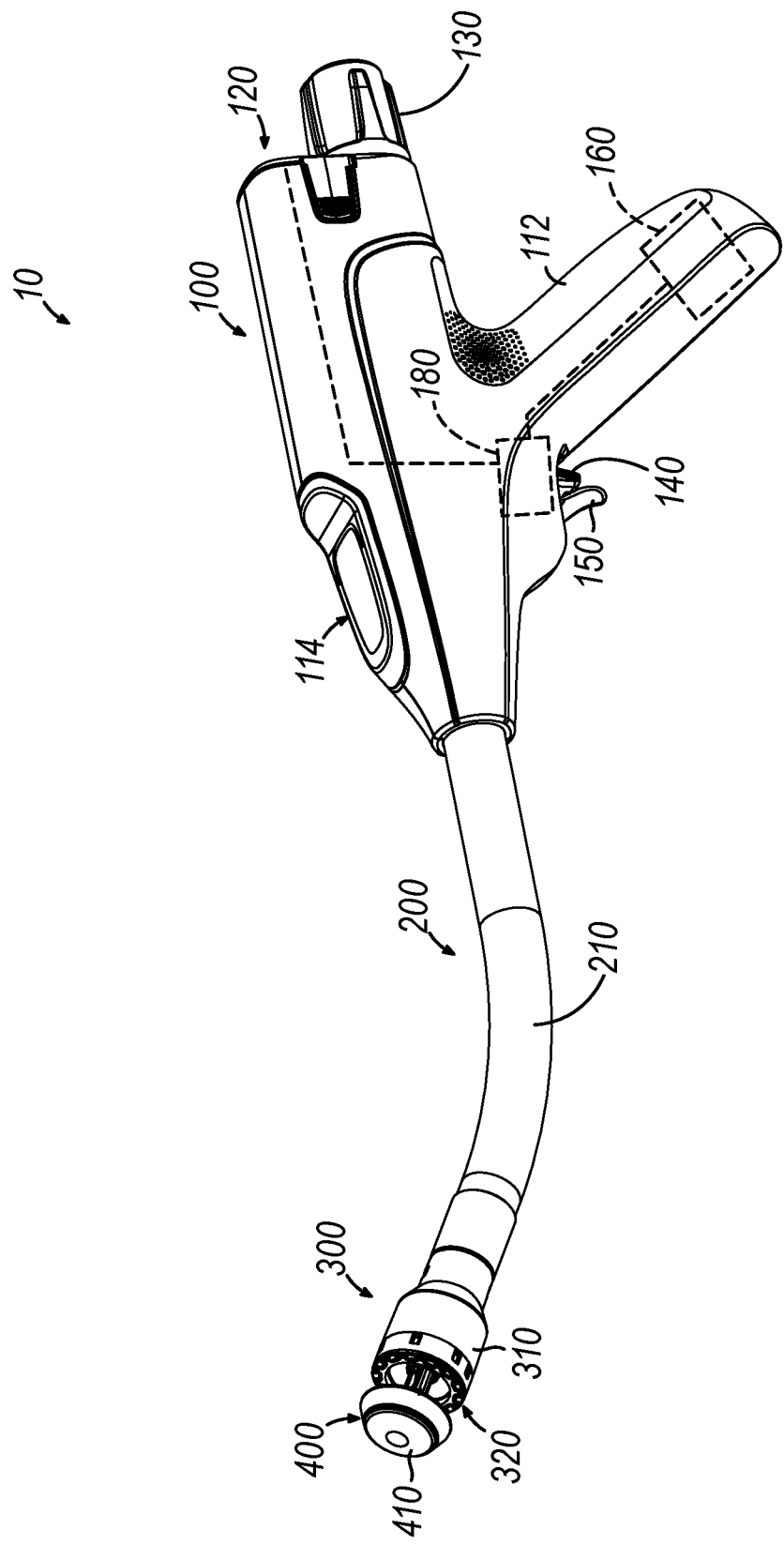
FIG. 1 depicts a perspective view of an exemplary circular surgical stapler that includes a handle assembly, a shaft assembly, and an end effector having a stapling head assembly and an anvil.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

For clarity of disclosure, the terms "proximal" and "distal" are defined herein relative to a surgeon, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms such as "top," "bottom," "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

Furthermore, the terms "about," "approximately," and the like as used herein in connection with any numerical values or ranges of values are intended to encompass the exact value(s) referenced as well as a suitable tolerance that enables the referenced feature or combination of features to function for the intended purpose described herein.

I. Overview of Exemplary Circular Surgical Stapling Instrument

Figure 2:
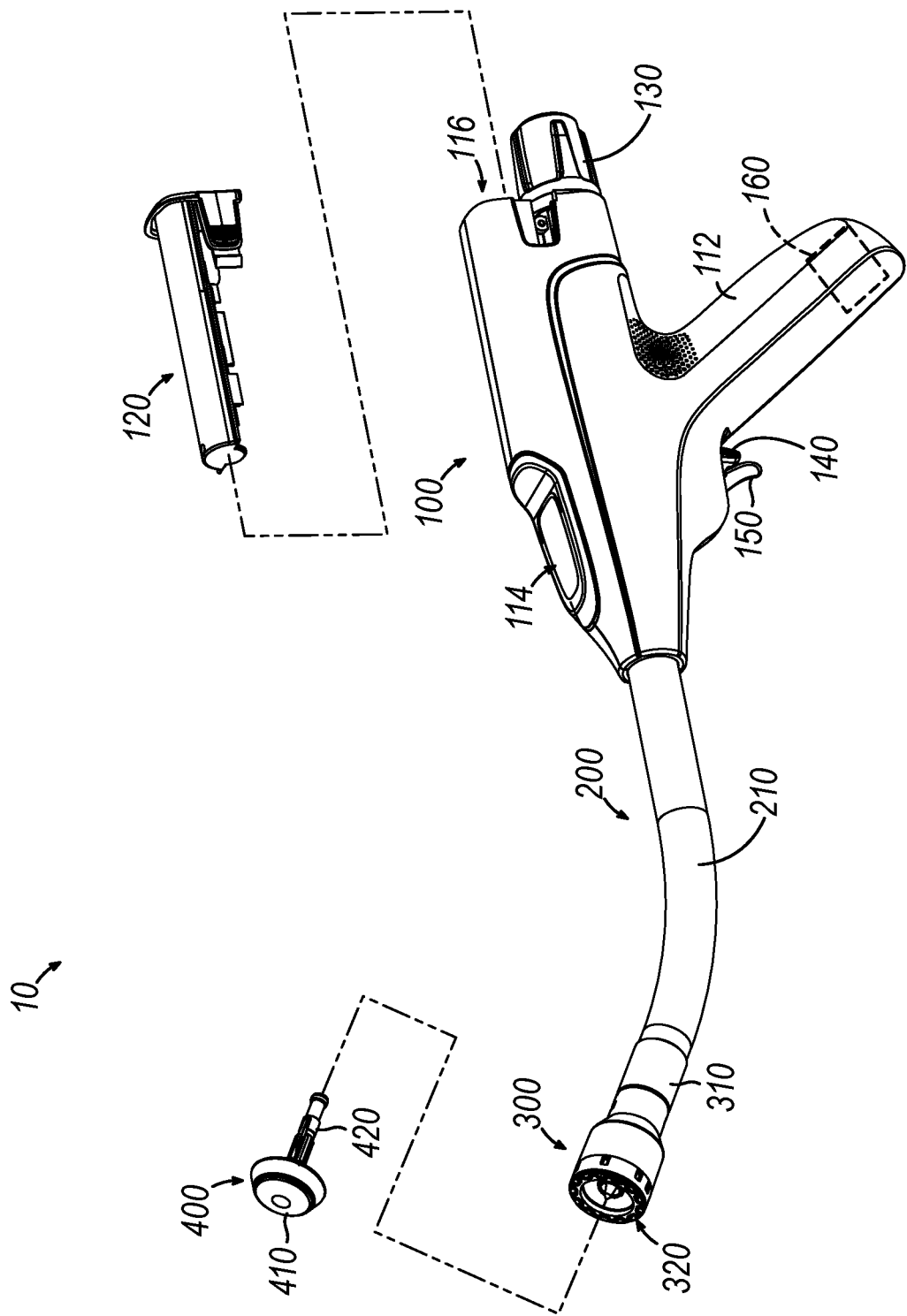
FIG. 2 depicts a perspective view of the circular stapler of FIG. 1, with a battery pack removed from the handle assembly and the anvil separated from the stapling head assembly.

FIGS. 1-2 depict an exemplary circular surgical stapling instrument (10) that may be used to provide an end-to-end, side-to-side, or end-to-side anastomosis between two sections of an anatomical lumen such as a portion of a patient's digestive tract. Instrument (10) of this example includes a body assembly in the form of a handle assembly (100), a shaft assembly (200) extending distally from handle assembly (100), a stapling head assembly (300) at a distal end of shaft assembly (200), and an anvil (400) configured to releasably couple and cooperate with stapling head assembly (300) to clamp, staple, and cut tissue. Instrument (10) further includes a removable battery pack (120) operable to provide electrical power to a motor (160) housed within handle assembly (100), as will be described in greater detail below.

As shown in FIGS. 1-2 and as will be described in greater detail below, anvil (400) is configured to removably couple with shaft assembly (200), adjacent to stapling head assembly (300). As will also be described in greater detail below, anvil (400) and stapling head assembly (300) are configured to cooperate to manipulate tissue in three ways, including clamping the tissue, cutting the tissue, and stapling the tissue. A rotatable knob (130) at the proximal end of handle assembly (100) is rotatable to provide precise clamping of the tissue between anvil (400) and stapling head assembly (300). When a safety trigger (140) of handle assembly (100) is pivoted away from a firing trigger (150) of handle assembly (100), firing trigger (150) may be actuated to thereby provide cutting and stapling of the clamped tissue.

A. Exemplary Anvil

Figure 3:
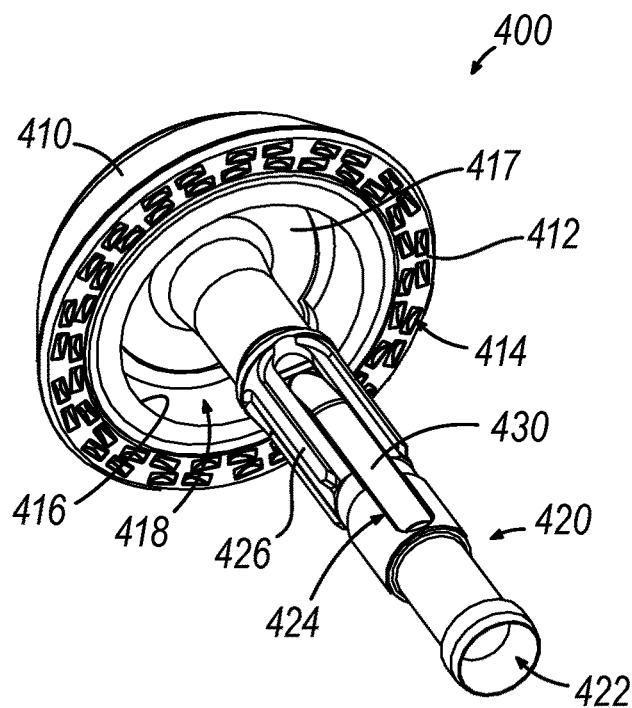
FIG. 3 depicts a perspective view of the anvil of the circular stapler of FIG. 1.

As best seen in FIG. 3, anvil (400) of the present example comprises a head (410) and a shank (420). Head (410) includes a proximal stapling surface (412) that defines a plurality of staple forming pockets (414). Staple forming pockets (414) are arranged in two concentric annular arrays in the present example. Staple forming pockets (414) are configured to deform staples as the staples are driven into staple forming pockets (414). Proximal stapling surface (412) terminates at an inner edge (416), which defines an outer boundary of an annular recess (418) surrounding shank (420). A breakable washer (417) is positioned within annular recess (418) and is configured to provide the operator with a tactile and audible indication that a distal firing stroke has been completed, in addition to serving as a cutting board, as described in greater detail below.

Shank (420) defines a bore (422) and includes a pair of pivoting latch members (430). Latch members (430) are positioned within bore (422) such that distal ends (434) are positioned at the proximal ends of lateral openings (424), which are formed through the sidewall of shank (420). Latch members (430) thus act as retaining clips. This allows anvil (400) to be removably secured to an actuatable closure member in the form of a trocar (330) of stapling head assembly (300), as will be described in greater detail below. Shank (420) of anvil (400) and trocar (330) of stapling head assembly (300) thus cooperate with one another as coupling members.

B. Exemplary Stapling Head Assembly

Figure 4:
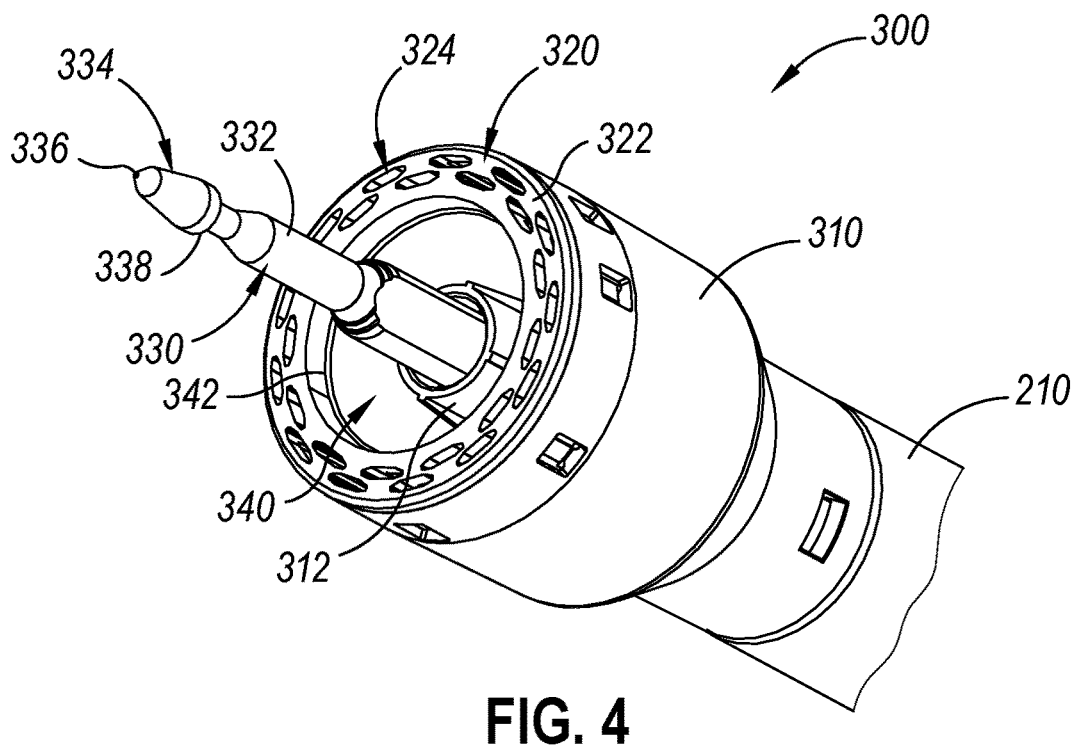
FIG. 4 depicts a perspective view of the stapling head assembly of the circular stapler of FIG. 1.
Figure 5:
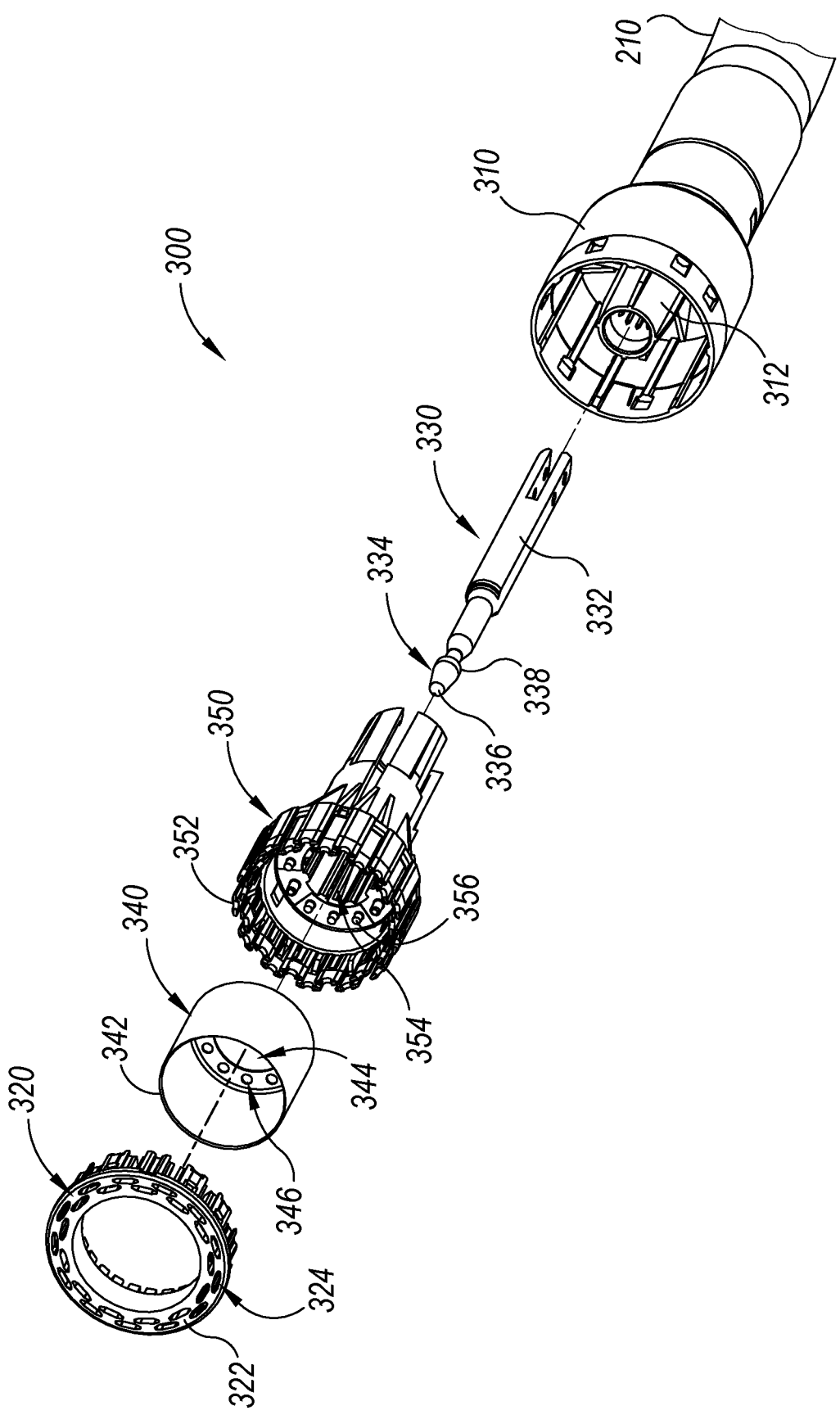
FIG. 5 depicts an exploded perspective view of the stapling head assembly of FIG. 4.

As best seen in FIGS. 4 and 5, stapling head assembly (300) of the present example is coupled to a distal end of shaft assembly (200) and comprises a tubular body member (310) and a staple driver member (350) slidably housed therein. Body member (310) includes a distally extending cylindraceous inner core member (312) positioned coaxially therein. Body member (310) is fixedly secured to an outer sheath (210) of shaft assembly (200), and body member (310) and outer sheath (210) thus serve together as a mechanical ground for stapling head assembly (300).

Trocar (330) is positioned coaxially within inner core member (312) of body member (310). As will be described in greater detail below, trocar (330) is operable to translate distally and proximally relative to body member (310) in response to rotation of knob (130) relative to casing (110) of handle assembly (100). Trocar (330) comprises a shaft (332) and a head (334). Head (334) includes a pointed tip (336) and a radially inwardly extending proximal surface (338). Head (334) and the distal portion of shaft (332) are configured for insertion into bore (422) of anvil (400). Proximal surface (338) and latch shelves (436) have complementary positions and configurations such that latch shelves (436) engage proximal surface (338) when shank (420) of anvil (400) is fully seated on trocar (330). Anvil (400) is thus secured to trocar (330) through a snap fit provided by latch members (430).

Staple driver member (350) is operable to actuate longitudinally within body member (310) in response to activation of motor (160) as will be described in greater detail below. As shown best in FIG. 5, staple driver member (350) of the present example includes two distally presented concentric annular arrays of staple drivers (352). Staple drivers (352) are arranged to correspond with the arrangement of staple forming pockets (414) of anvil (400). Thus, each staple driver (352) is configured to drive a corresponding staple distally into a corresponding staple forming pocket (414) when stapling head assembly (300) is actuated (or "fired"). Staple driver member (350) also defines a bore (354) that is configured to coaxially and slidably receive core member (312) of body member (310). An annular array of studs (356) project distally from a distally presented surface surrounding bore (354).

A cylindraceous knife member (340) is coaxially positioned within a distally-opening central recess of staple driver member (350) that communicates with bore (354). Knife member (340) includes a distally presented, sharp circular cutting edge (342). Knife member (340) is sized such that knife member (340) defines an outer diameter that is just smaller than the diameter defined by the radially inner-most surfaces of the inner annular array of staple drivers (352). Knife member (340) also defines a central opening that is configured to coaxially receive core member (312) of body member (310). An annular array of openings (346) formed in knife member (340) is configured to mate with the annular array of studs (356) of staple driver member (350), such that knife member (340) is fixedly secured to staple driver member (350) via studs (356) and openings (346).

An annular deck member (320) is fixedly secured to a distal end of body member (310). Deck member (320) includes a distally presented stapling surface in the form of a deck surface (322) having two concentric annular arrays of staple openings (324). Staple openings (324) are arranged to align with the arrangement of staple drivers (352) of staple driver member (350) and staple forming pockets (414) of anvil (400) described above. Each staple opening (324) is configured to slidably receive and provide a pathway for a corresponding staple driver (352) to drive a corresponding staple distally through deck member (320) and into a corresponding staple forming pocket (414) when stapling head assembly (300) is actuated. As best seen in FIG. 4, deck member (320) has a central opening that defines an inner diameter that is just slightly larger than the outer diameter defined by knife member (340). Deck member (320) is thus configured to permit knife member (340) to translate longitudinally through the central opening concurrently with longitudinal translation of staple driver member (350). In particular, knife member (340) is configured to actuate relative to deck member (340) between a proximal retracted position and a distal extended position, where cutting edge (342) is proximal to deck surface (322) in the proximal retracted position and distal to deck surface (322) in the distal extended position.

C. Exemplary Shaft Assembly

Figure 6:
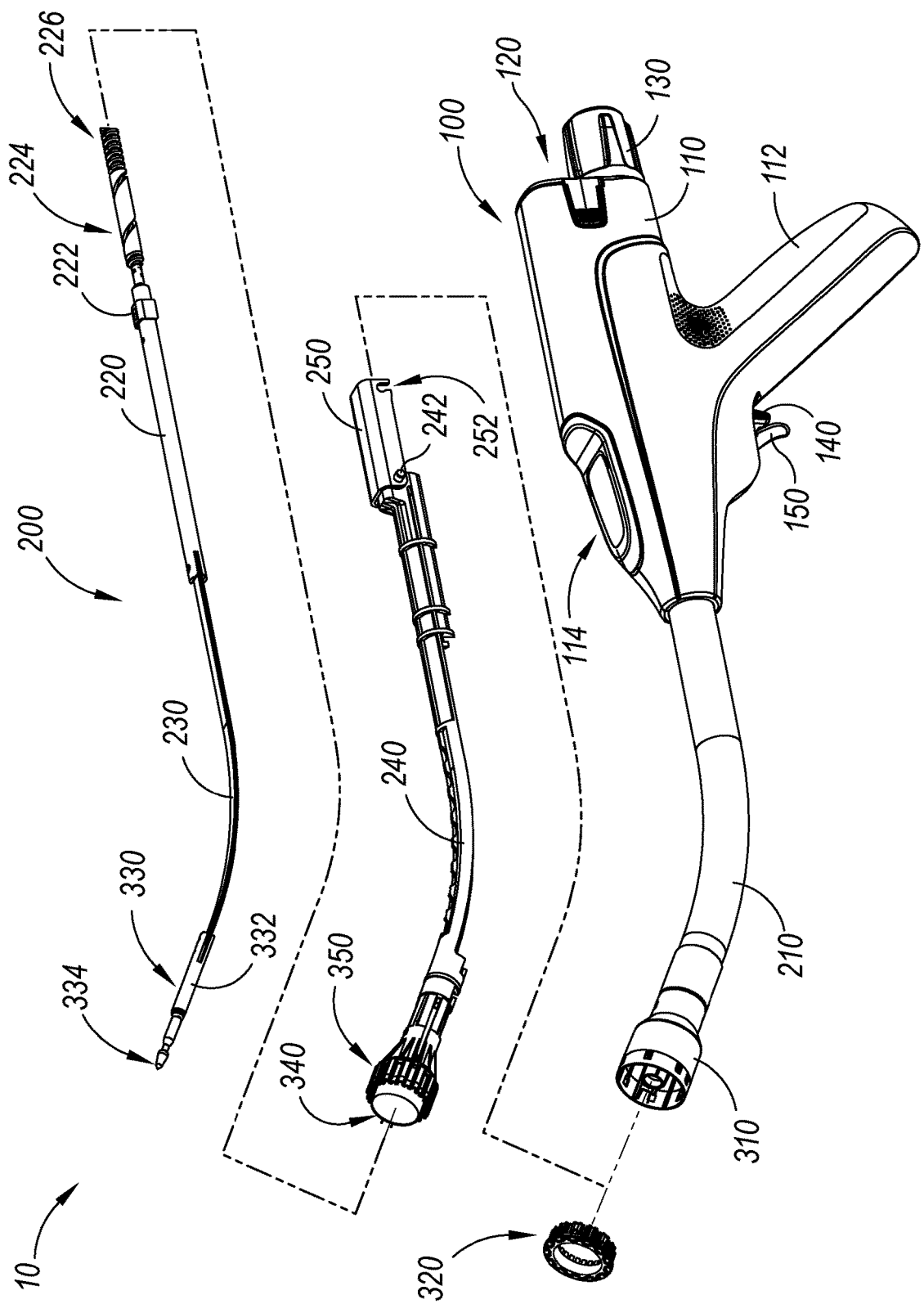
FIG. 6 depicts an exploded perspective view of the circular stapler of FIG. 1, with portions of the shaft assembly shown separated from each other.

FIG. 6 shows various components of shaft assembly (200), which operatively couple components of stapling head assembly (300) with components of handle assembly (100). In particular, and as noted above, shaft assembly (200) includes an outer sheath (210) that extends between handle assembly (100) and body member (310) and includes a medial portion that extends along a curved path.

Shaft assembly (200) further includes a trocar actuation rod (220) having a proximal end operatively coupled with rotatable knob (130) and a distal end coupled with a flexible trocar actuation band assembly (230), the assembly of which is slidably housed within outer sheath (210). The distal end of trocar actuation band assembly (230) is fixedly secured to the proximal end of trocar shaft (332), such that trocar (330) will translate longitudinally relative to outer sheath (210) in response to translation of trocar actuation band assembly (230) and trocar actuation rod (220) relative to outer sheath (210), which occurs in response to rotation of rotatable knob (130). A clip (222) is fixedly secured to trocar actuation rod (220) and is configured to cooperate with complementary features within handle assembly (100) to prevent trocar actuation rod (220) from rotating within handle assembly (100) while still permitting trocar actuation rod (220) to translate longitudinally within handle assembly (100). Trocar actuation rod (220) further includes a section of coarse helical threading (224) and a section of fine helical threading (226) proximal to coarse helical threading (224), which are configured to control a rate of longitudinal advancement of trocar actuation rod (220), as described in greater detail below.

Shaft assembly (200) further includes a stapling head assembly driver (240) that is slidably housed within outer sheath (210) and about the combination of trocar actuation rod (220) and trocar actuation band assembly (230). Stapling head assembly driver (240) includes a distal end that is fixedly secured to the proximal end of staple driver member (350), a proximal end secured to a drive bracket (250) via a pin (242), and a flexible section disposed therebetween. It should therefore be understood that staple driver member (350) will translate longitudinally relative to outer sheath (210) in response to translation of stapling head assembly driver (240) and drive bracket (250) relative to outer sheath (210).

D. Exemplary Handle Assembly and User Input Features

As shown in FIG. 1, handle assembly (100) includes a casing (110) having a lower portion that defines an obliquely oriented pistol grip (112) and an upper portion that supports a user interface feature (114) and releasably receives a battery pack (120), as described in greater detail below. Handle assembly (100) further includes several features that are operable to actuate anvil (400) and stapling head assembly (300). In particular, handle assembly (100) includes a rotatable knob (130), a safety trigger (140), a firing trigger (150), a motor (160), and a motor activation module (180). Knob (130) is coupled with trocar actuation rod (220) via a nut (not shown), such that coarse helical threading (224) will selectively engage a thread engagement feature within the interior of the nut; and such that fine helical threading (226) will selectively engage a thread engagement feature within the interior of knob (130). These complementary structures are configured such that trocar actuation rod (220) will first translate proximally at a relatively slow rate, and then translate proximally at a relatively fast rate, in response to rotation of knob (130).

It should be understood that when anvil (400) is coupled with trocar (330), rotation of knob (130) will provide corresponding translation of anvil (400) relative to stapling head assembly (300). It should also be understood that knob (130) may be rotated in a first angular direction (e.g., clockwise) to retract anvil (400) proximally toward stapling head assembly (300); and in a second angular direction (e.g., counterclockwise) to extend anvil (400) distally away from stapling head assembly (300). Knob (130) may thus be used to adjust a gap distance (d) between opposing stapling surfaces (412, 322) of anvil (400) and stapling head assembly (300) until a suitable gap distance (d) has been achieved, for example as shown in FIG. 7C described below.

Firing trigger (150) is operable to activate motor (160) to thereby actuate stapling head assembly (300) to staple and cut tissue clamped between anvil (400) and stapling head assembly (300). Safety trigger (140) is operable to selectively block actuation of firing trigger (150) based on the longitudinal position of anvil (400) in relation to stapling head assembly (300). Handle assembly (100) also includes components that are operable to selectively lock out both triggers (140, 150) based on the position of anvil (400) relative to stapling head assembly (300). For instance, safety trigger (140) may be blocked from rotating from an engaged position to a disengaged position until the position of anvil (400) relative to stapling head assembly (300) is within a predefined range. Accordingly, until the anvil position is within the predefined range, actuation of firing trigger (150) is blocked by safety trigger (140), thereby inhibiting firing of stapling head assembly (300).

Firing trigger (150) is operable to actuate a switch of motor activation module (180) (FIG. 1) when firing trigger (150) is pivoted proximally to a fired position. Motor activation module (180) is in communication with battery pack (120) and motor (160), such that motor activation module (180) is configured to provide activation of motor (160) with electrical power from battery pack (120) in response to firing trigger (150) actuating the switch of motor activation module (180). Thus, motor (160) will be activated when firing trigger (150) is pivoted. This activation of motor (160) will actuate stapling head assembly (300) via drive bracket (250), as described in greater detail below.

E. Exemplary Anastomosis Procedure with Circular Stapling Instrument

FIGS. 7A-7E show instrument (10) being used to form an anastomosis (70) between two tubular anatomical structures (20, 40). By way of example only, the tubular anatomical structures (20, 40) may comprise sections of a patient's esophagus, colon, or other portions of the patient's digestive tract, or any other tubular anatomical structures.

Figure 7A:
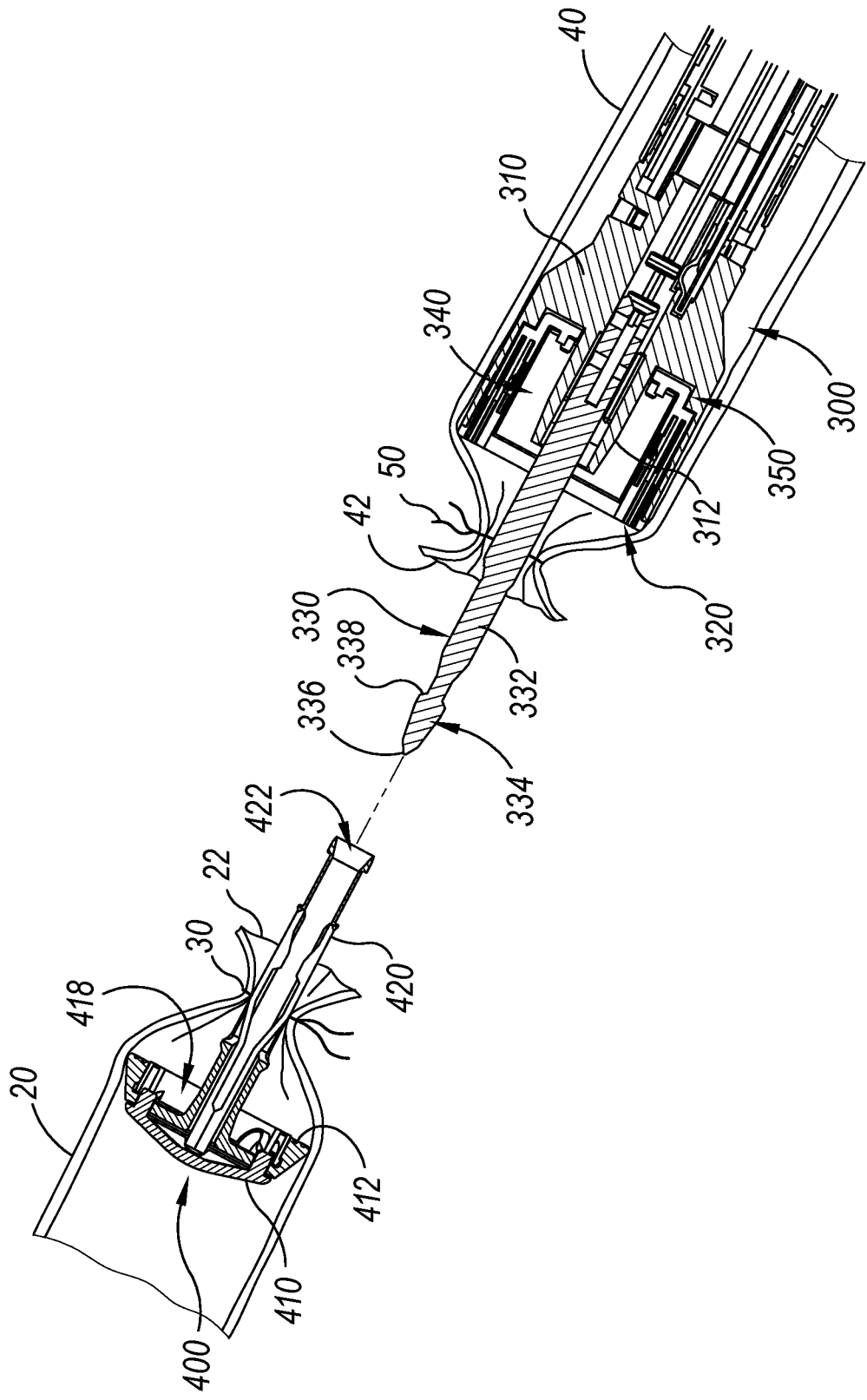
FIG. 7A depicts a cross-sectional side view of the anvil of FIG. 3 positioned within a first section of a digestive tract and the stapling head assembly of FIG. 4 positioned within a separate second section of the digestive tract, with the anvil separated from the stapling head assembly.

As shown in FIG. 7A, anvil (400) is positioned in one tubular anatomical structure (20) and stapling head assembly (300) is positioned in another tubular anatomical structure (40). As shown in FIG. 7A, anvil (400) is positioned in tubular anatomical structure (20) such that shank (420) protrudes from the open severed end (22) of tubular anatomical structure (20). In the present example, purse-string suture (30) is provided about a mid-region of shank (420) to generally secure the position of anvil (400) in tubular anatomical structure (20). Stapling head assembly (300) is positioned in tubular anatomical structure (40) such that trocar (330) protrudes from the open severed end (42) of tubular anatomical structure (20). A purse-string suture (50) is provided about a mid-region of shaft (332) to generally secure the position of stapling head assembly (300) in tubular anatomical structure (40). Stapling head assembly (300) is then urged distally to ensure that stapling head assembly (300) is fully seated at the distal end of tubular anatomical structure (40).

Figure 7B:
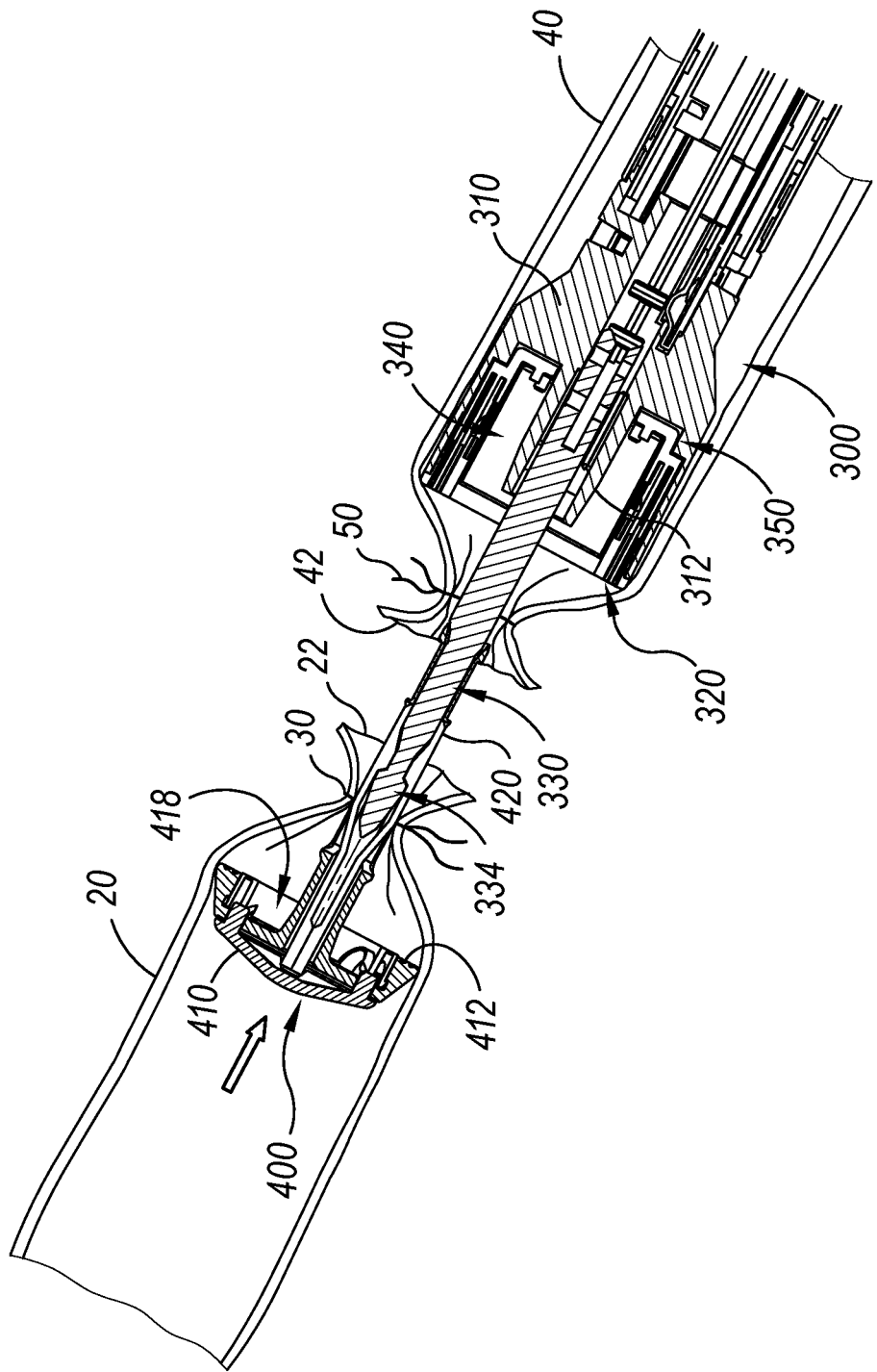
FIG. 7B depicts a cross-sectional side view of the anvil of FIG. 3 positioned within the first section of the digestive tract and the stapling head assembly of FIG. 4 positioned within the separate second section of the digestive tract, with the anvil secured to the stapling head assembly.
Figure 7C:
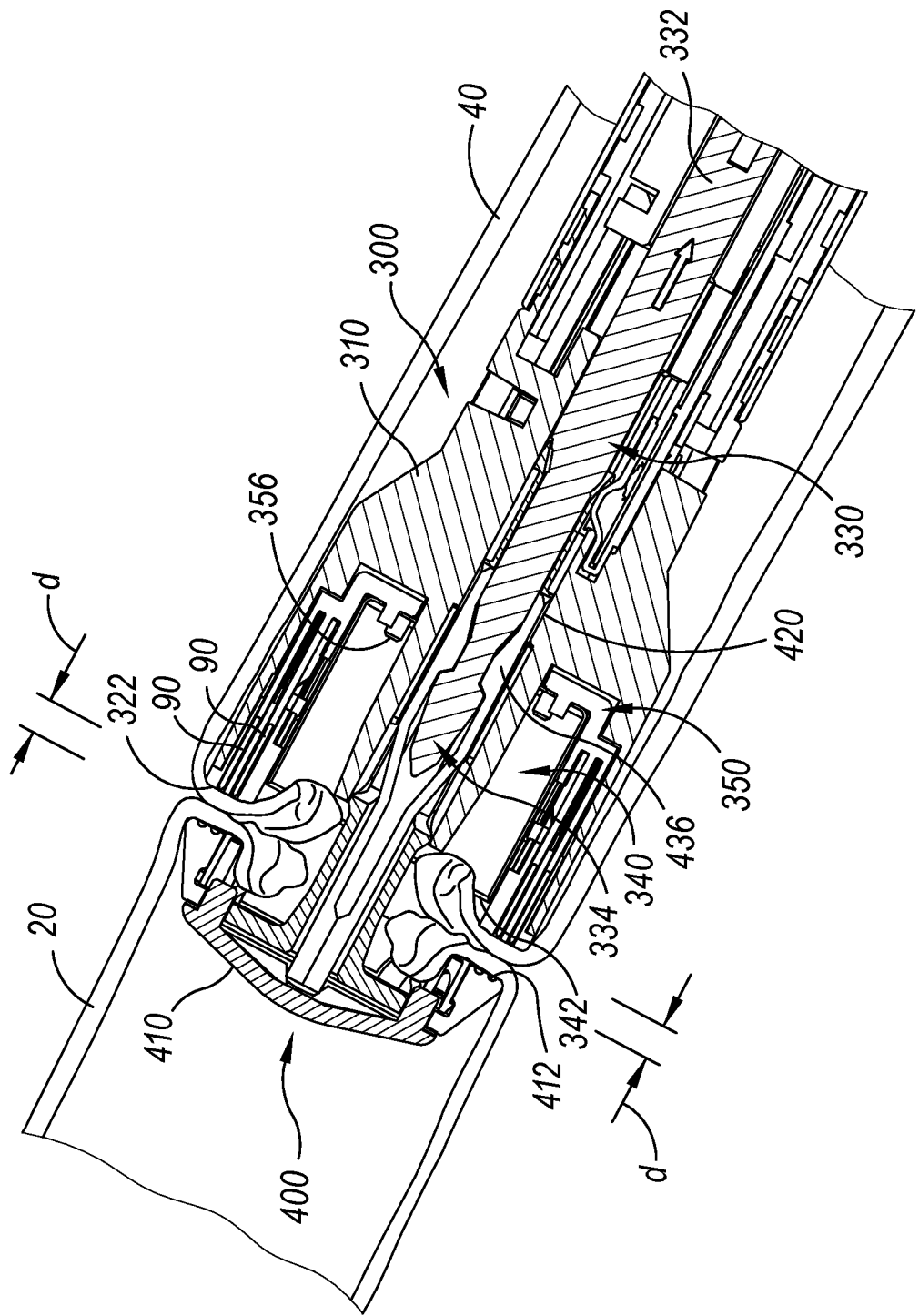
FIG. 7C depicts a cross-sectional side view of the anvil of FIG. 3 positioned within the first section of the digestive tract and the stapling head assembly of FIG. 4 positioned within the separate second section of the digestive tract, with the anvil retracted toward the stapling head assembly to thereby clamp tissue between the anvil and the stapling head assembly.

Next, anvil (400) is secured to trocar (330) by inserting trocar (330) into bore (422) as shown in FIG. 7B. Latch members (430) of anvil (400) engage head (334) of trocar (330), thereby providing a secure fit between anvil (400) and trocar (330). The operator then rotates knob (130) while holding casing (110) stationary via pistol grip (112). This rotation of knob (130) causes trocar (330) and anvil (400) to retract proximally. As shown in FIG. 7C, this proximal retraction of trocar (330) and anvil (400) compresses the tissue of tubular anatomical structures (20, 40) between surfaces (412, 322) of anvil (400) and stapling head assembly (300). As this occurs, the operator may observe the tactile resistance or feedback via knob (130) while turning knob (130), with such tactile resistance or feedback indicating that the tissue is being compressed. As the tissue is being compressed, the operator may visually observe the position of an indicator needle (not shown) within user interface feature (114) of handle assembly (100) to determine whether the gap distance (d) between opposing surfaces (412, 322) of anvil (400) and stapling head assembly (300) is appropriate; and make any necessary adjustments via knob (130).

Once the operator has appropriately set the gap distance (d) via knob (130), the operator pivots safety trigger (140) toward pistol grip (112) to enable actuation of firing trigger (150). The operator then pivots firing trigger (150) toward pistol grip (112), thus causing firing trigger (150) to actuate the switch of motor activation module (180) and thereby activate motor (160) to rotate. This rotation of motor (160) causes actuation (or "firing") of stapling head assembly (300) by actuating drive bracket (250) distally to thereby drive knife member (340) and staple driver member (350) distally together, as shown in FIG. 7D.

As knife member (340) translates distally, cutting edge (342) of knife member (340) cuts excess tissue that is positioned within annular recess (418) of anvil (400) and the interior of knife member (340). Additionally, washer (417) positioned within annular recess (418) of anvil (400) is broken by knife member (340) when the knife member (340) completes a full distal range of motion from the position shown in FIG. 7C to the position shown in FIG. 7D. It should be understood that washer (417) may also serve as a cutting board for knife member (340) to assist in cutting of tissue.

Figure 7D:
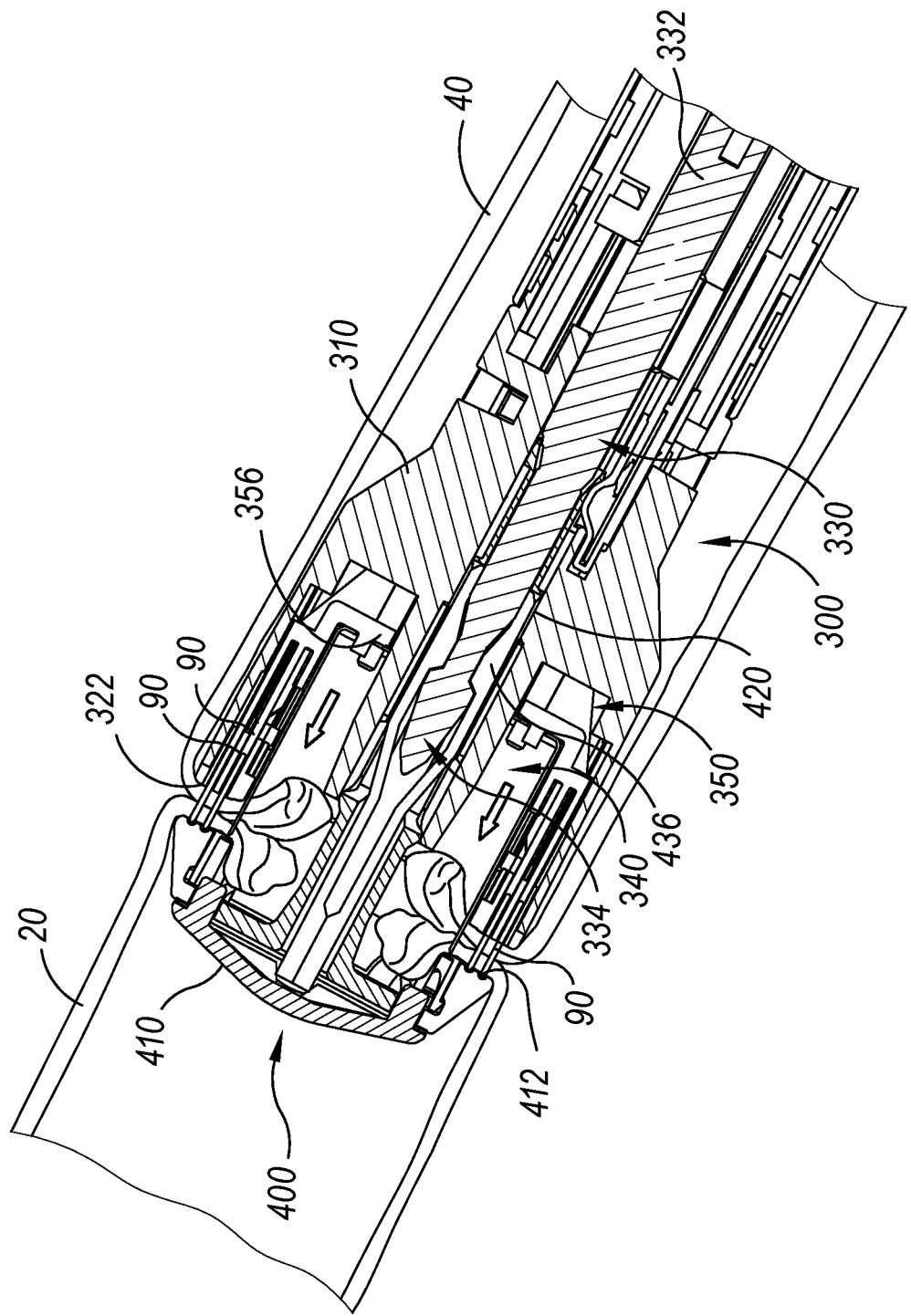
FIG. 7D depicts a cross-sectional side view of the anvil of FIG. 3 positioned within the first section of the digestive tract and the stapling head assembly of FIG. 4 positioned within the second section of the digestive tract, with the stapling head assembly actuated to sever and staple the clamped tissue and thereby joining the first and second sections of the digestive tract.

As staple driver member (350) translates distally from the position shown in FIG. 7C to the position shown in FIG. 7D, staple driver member (350) drives staples (90) through the tissue of tubular anatomical structures (20, 40) and into staple forming pockets (414) of anvil (400). Staple forming pockets (414) deform the driven staples (90) into a "B" shape or a three-dimensional shape, for example, such that the formed staples (90) secure the ends of tissue together, thereby coupling tubular anatomical structure (20) with tubular anatomical structure (40).

Figure 7E:
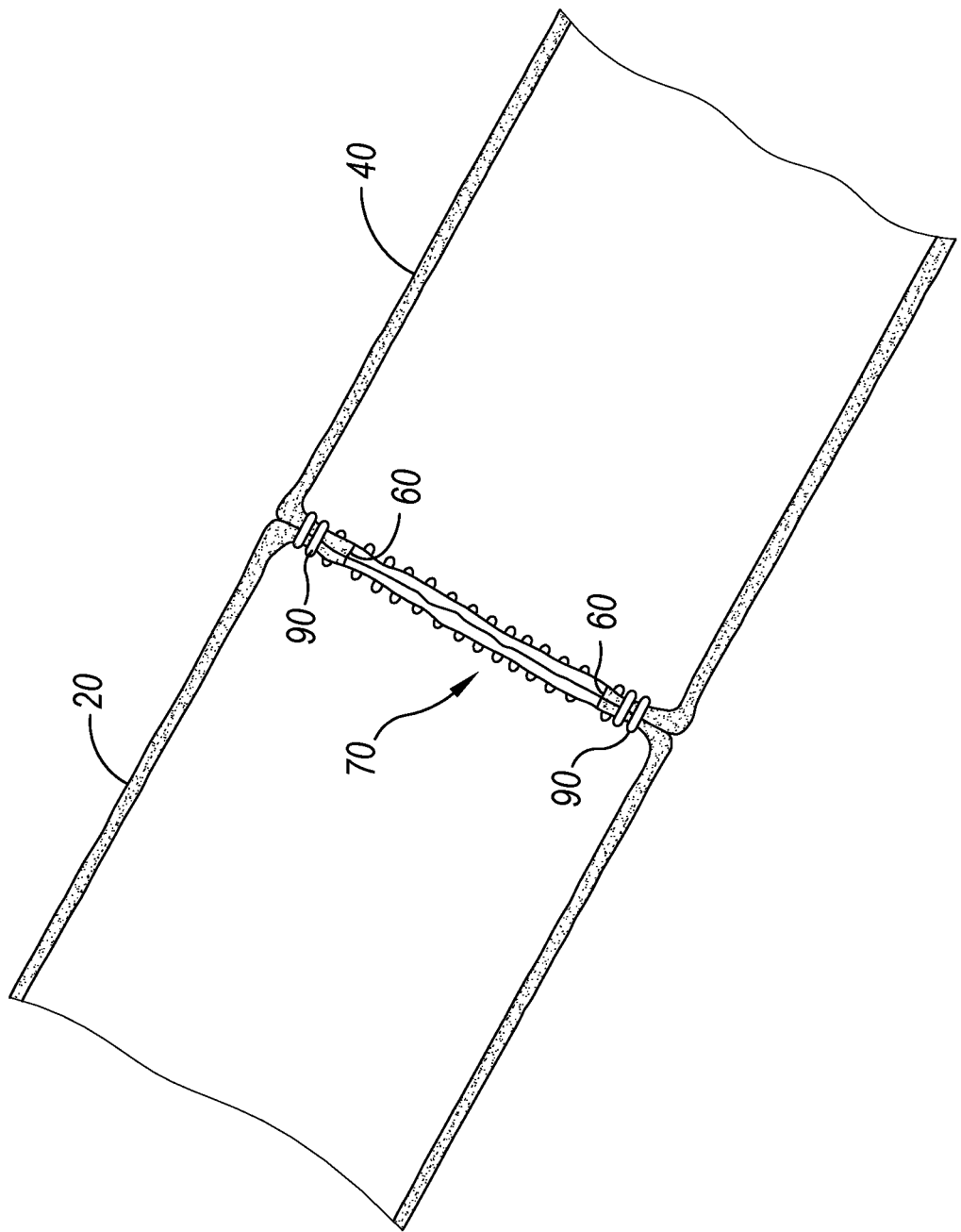
FIG. 7E depicts a cross-sectional side view of the first and second sections of the digestive tract of FIG. 7A joined together at an end-to-end anastomosis formed with the circular stapler of FIG. 1.

After the operator has actuated (or "fired") stapling head assembly (300) as shown in FIG. 7D, the operator rotates knob (130) to drive anvil (400) distally away from stapling head assembly (300), thereby increasing the gap distance (d) to facilitate release of the tissue between surfaces (412, 322). The operator then removes instrument (10) from the patient, with anvil (400) still secured to trocar (330). With instrument (10) removed, the tubular anatomical structures (20, 40) are left secured together by two annular arrays of staples (90) at an anastomosis (70) as shown in FIG. 7E. The inner diameter of the anastomosis (70) is defined by the severed edge (60) left by knife member (340).

II. Exemplary End Effectors Having Non-Circular Features

As noted above, the inner diameter of anastomosis (70) formed by instrument (10) is defined by the outer diameter of knife member (340). Because knife member (340) is smaller than the inner diameters of tubular anatomical structures (20, 40), the resulting diameter of anastomosis (70) is generally smaller than that of each tubular anatomical structure (20, 40). Additionally, the configuration of formed staples (90) may inhibit the ability of anastomosis (70) to expand radially.

In some procedures, it may be desirable to form an anastomosis (70) of enlarged diameter and/or to enable annular arrays of formed staples (90) to expand radially, thereby minimizing strictures, enabling better peristalsis, and minimizing local tension in and resulting damage to the joined portions of tubular anatomical structures (20, 40). Accordingly, in some such instances, it may be desirable to configure a stapling head assembly (520) and an anvil (550) with a knife member (510) having a shape that enables formation of such an anastomosis and/or patterns of formed staples (90). Exemplary versions of such features are described in greater detail below.

Figure 8:
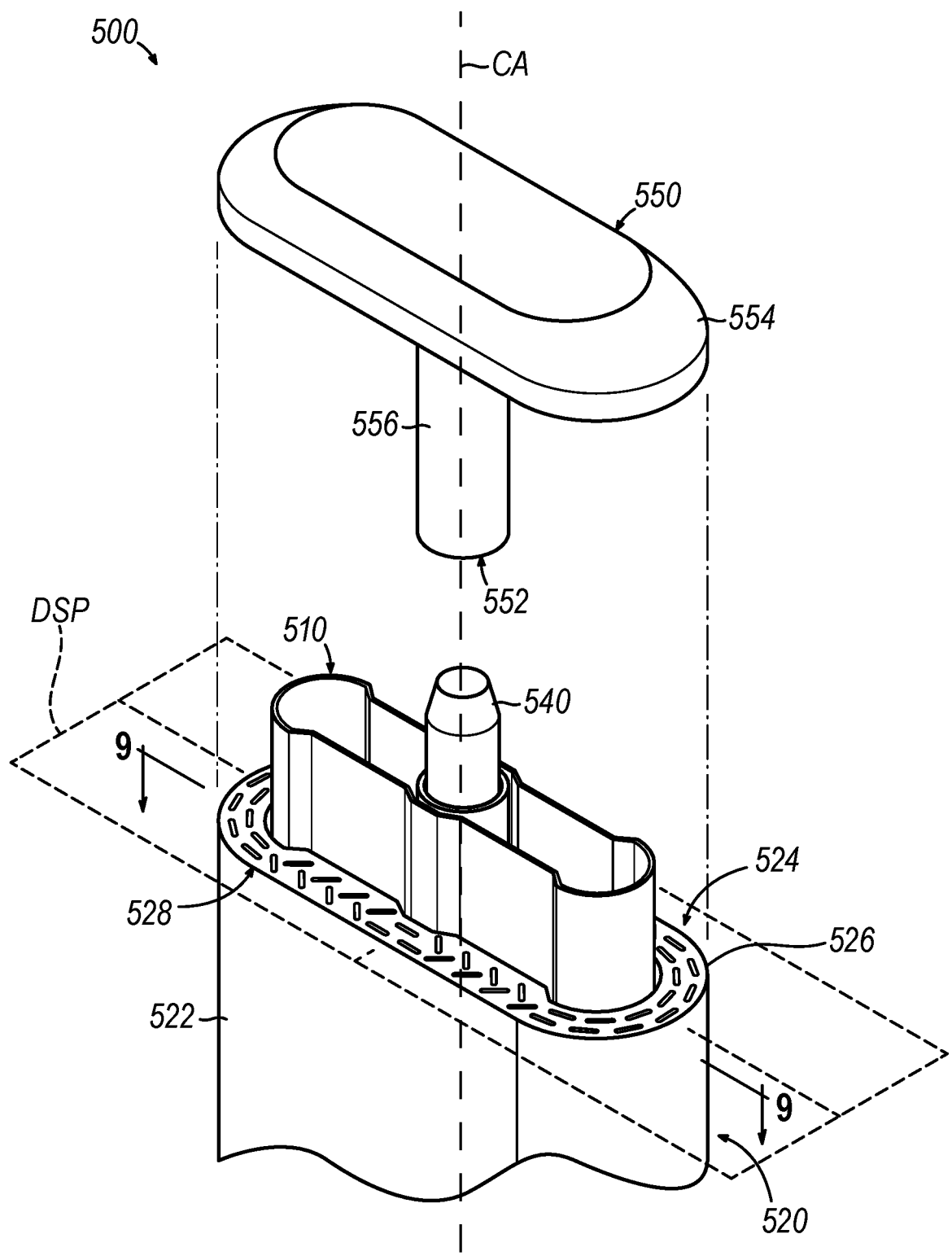
FIG. 8 depicts a perspective view of another exemplary end effector including a stapling head assembly and anvil for use with the circular stapler of FIG. 1.

A. Exemplary Non-Circular End Effector Having Oval Knife Member with Arcuate End Portions FIG. 8 shows an exemplary non-circular end effector (500) having a stapling head assembly (520) and an anvil (550) configured to releasably couple with stapling head assembly (520). It will be appreciated that stapling head assembly (520) and anvil (550) are similar in structure and function to stapling head assembly (300) and anvil (400) described above except as otherwise described. In particular, and as described in greater detail below, stapling head assembly (520) of the present example includes an oval knife member (510) with arcuate end portions (538) configured to create an anastomosis between tubular anatomical structures (20, 40) of a patient having an elongated transverse cross-sectional shape.

Stapling head assembly (520) of end effector (500) includes a housing in the form of a body member (522). Body member (522) includes a deck member (524) having a distally facing deck surface (526), and a knife member (510) at least partially disposed within body member (522). Body member (522) extends distally along a longitudinal axis defined as a central axis (CA) from a distal end of shaft assembly (200) and further includes a staple driver member (not shown) slidably housed therein similar to stapler driver member (350) of stapling head assembly (300). Body member (522) is fixedly secured to an outer sheath (210) of shaft assembly (200), and body member (522) and outer sheath (210) thus serve together as a mechanical ground for stapling head assembly (520).

A coupling feature in the form of a trocar (540) is positioned coaxially within an inner core member (not shown) of stapling head assembly (520). Like trocar (330), trocar (540) is operable to translate distally and proximally relative to body member (522) in response to rotation of knob (130) relative to casing (110) of handle assembly (100). Trocar (540) is configured for insertion into anvil (550) through bore (552) and latches to anvil (550) like trocar (330).

Similar to anvil (400) described above, anvil (550) includes a head (554) and shank (556) extending proximally from head (554) and is configured to releasably couple with trocar (540) of stapling head assembly (520). Head (554) has an elongate shape similar to an exterior profile of body member (522) of stapling head assembly (520) and a low-profile shape that defines a proximal surface (558) having a plurality of staple forming pockets (not shown) similar to staple forming pockets (414) described above. Proximal surface (558) is configured to cooperate with deck surface (526) to clamp and staple tissue. In the present version, anvil (550) further includes a washer (not shown) recessed within anvil (550) of suitable shape that functions in a manner similar to washer (417) described above.

Figure 9:
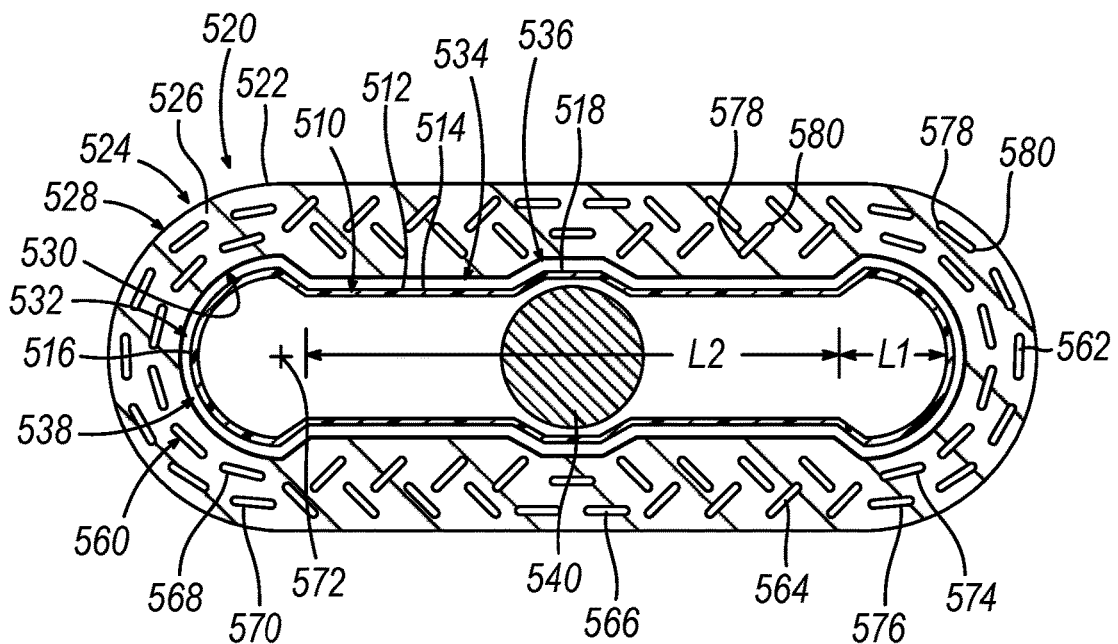
FIG. 9 depicts a top plan view of the stapling head assembly of FIG. 8.

As shown in FIG. 9, deck member (524) includes a distally presented stapling surface in the form of a deck surface (526). Deck surface (526) has a non-circular configuration with an exterior perimeter (528) defining a first non-circular shape and an interior perimeter (530) defining a second non-circular shape that is different than the first non-circular shape. Exterior perimeter (528) and interior perimeter (530) lie within a deck surface plane (DSP) that orthogonally intersects central axis (CA) of stapling head assembly (520), as shown in FIG. 8. Exterior perimeter (528) has an oval, elongate first non-circular shape. Interior perimeter (530) defines a lumen (532) within deck member (524) and has a second non-circular shape.

As shown in FIG. 9, interior perimeter (530) of deck surface (526) includes four linear medial portions (534), two outwardly extending central portions (536) each interconnecting an adjacent pair of linear medial portions (534), and two arcuate end portions (538) each interconnecting an opposed pair of linear medial portions (534). Central portions (536) are diametrically opposed from one another about central axis (CA) and are in the form of radially outwardly extending angled step features configured to provide clearance for proximal and distal translation of trocar (540) therebetween. In other versions, interior perimeter (530) may include two linear medial portions (534) and two arcuate end portions (538), with no intervening outwardly extending central portions (536) of the type shown herein.

Deck surface (526) of the present version has a narrower transverse width, measured between interior and exterior perimeters (530, 528), at arcuate end portions (538) and at central portions (536), and a thicker transverse width along linear portions (534). Accordingly, interior perimeter (530) has the shape of a dog bone, with an elongate central shaft feature defined by linear medial portions (534) and outwardly extending central portions (536) in combination, and a pair of bulbous end features defined by arcuate end portions (538). More specifically, the dog bone shape has a first arcuate end portion (538) on a first side of central axis (CA), and a second arcuate end portion (538) on an opposed second side of central axis (CA). In other versions, interior perimeter (530) of deck surface (526) may define various other suitable shapes, such as a flower pedal shape where interior perimeter (530) further includes a linear angled portion (not shown) that further transitions between linear medial portions (534) and arcuate end portions (538).

Deck surface (526) further includes a plurality of staple openings (560) configured to receive and house staples (not shown), similar to staples (90) described above. In the present example, staple openings (560) are arranged on deck surface (526) in a first array (562) of staple openings (560), a second array (564) of staple openings (560), and a third array (566) of staple openings (560). First array (562) of staple openings (560) is positioned along each of arcuate end portions (538); second array (564) of staple openings (560) is positioned along each of linear medial portions (534); and third array (566) of staple openings (560) is positioned along each of outwardly extending central portions (536). First array (562) of staple openings (560) is arranged with a different configuration than second array (564) of staple openings (560). Third array (566) of staple openings (560) is arranged with a similar configuration as first array (562) of staple openings (560).

First array (562) of staple openings (560) includes a first inner row (568) and a first outer row (570). Each of staple openings (560) in first array (562) extends tangentially to the respective arcuate end portion (538) about a respective end axis (572), which is central to the respective arcuate end portion (538). Each of staple openings (560) of first inner row (568) is staggered relative to each of staple openings (560) of first outer row (570), such that each staple opening (560) of inner row (568) is circumferentially offset from each staple opening (560) of outer row (570).

Second array (564) of staple openings (560) includes a second inner row (574) and a second outer row (576) angled perpendicularly to each other in a herringbone configuration. Each staple opening (560) includes a first end (578) and an opposed second end (580). Each staple opening (560) of second inner row (574) is oriented angularly relative to the corresponding linear portion (534) and an imaginary circumferential midline of deck surface (526) such that first end (578) of each staple opening (560) in second inner row (574) is closer to interior perimeter (530) that second end (580). Each staple opening (560) in second outer row (576) has an angular orientation that is opposite that of staple openings (560) of first inner row (568), whereinfirst end (578) of each staple opening (560) in second outer row (576) is closer to exterior perimeter (528) than the corresponding second end (580). This angular configuration of staple openings (560) in second arrays (564) may allow for outward radial expansion of the formed staple array deployed by deck member (524) at portions arranged along linear medial portions (534) of interior perimeter (530). This radial expandability of the formed staple array in combination with the overall elongate shape of the formed staple array may provide for an improved anastomosis that exhibits the benefits described above.

Knife member (510) of the present example has a distal knife edge (512) that defines an edge plane (not shown) that is parallel to deck surface plane (DSP) seen in FIG. 8 and orthogonally intersects central axis (CA) of stapling head assembly (520). Knife edge (512) has a non-circular, dog bone-like shape in the edge plane that complements the dog bone-like shape of interior perimeter (530) of deck surface (526) described above. More specifically, knife edge (512), similar to interior perimeter (530), includes four linear medial edge portions (514), a pair of arcuate end edge portions (516) diametrically opposed from one another about central axis (CA), and a pair of radially outwardly extending central edge portions (518) diametrically opposed from one another about central axis (CA) and interconnecting adjacent pairs of linear medial edge portions (514). In other versions, knife member (510) may be suitably sized and shaped to omit outwardly protruding central edge portions (518) such that arcuate end edge portions (516) are interconnected by an opposed pair of elongate linear edge portions.

As seen in FIG. 9, knife member (510) is suitably shaped and sized smaller than interior perimeter (530) of deck member (524) to provide for a uniform gap between the exterior perimeter of knife member (510) and interior perimeter (530) of deck member (524). In other words, the exterior perimeter of knife member (510), at least at knife edge (512), closely conforms to but is spaced inwardly from interior perimeter (530) of deck member such that the exterior surface of knife member (510) closely confronts but does not contact the interior surface of deck member (524). Accordingly, knife member (510) is operable to freely translate proximally and distally relative to deck member (524) during a distal firing stroke and a subsequent proximal retraction stroke.

As shown in FIG. 9, knife member (510) of the present version is shaped such that linear medial edge portions (514) and central edge portions (518) have a combined first length (L1) in a direction transverse to and extending through central axis (CA), and each end edge portion (516) has a second length (L2) in the same direction. First length (L1) is greater than second length (L2). In some versions, first length (L1) is greater than second length (L2) by a ratio of 3:1. Additionally, each arcuate end edge portion (516) may be formed with a semi-circular shape having a diameter that is equal to a transverse distance between radially outermost portions of opposed central edge portions (518), which distance may be greater than a transverse distance between each opposed pair of linear medial edge portions (514), thus providing the dog bone shape seen in FIGS. 8 and 9.

As described above, in other versions interior perimeter (530) of deck member (524) may be formed with various non-circular shapes, other than the dog bone shape shown and described herein, that are suitable to create an anastomosis (70) of enlarged diameter. It will be appreciated that in such alternative versions, knife member (510) may also be alternatively shaped such that knife edge (512) defines a shape that complements the shape of interior perimeter (530) of deck member (524). In some such versions, interior perimeter (530) of deck member (524) and knife edge (512) may each be formed with various types of elongate oval shapes. In other such versions, interior perimeter (530) of deck member (524) and knife edge (512) may each be formed with a flower pedal shape having a plurality of pointed or rounded lobes arranged circumferentially about central axis (CA), symmetrically or non-symmetrically.

Figure 10:
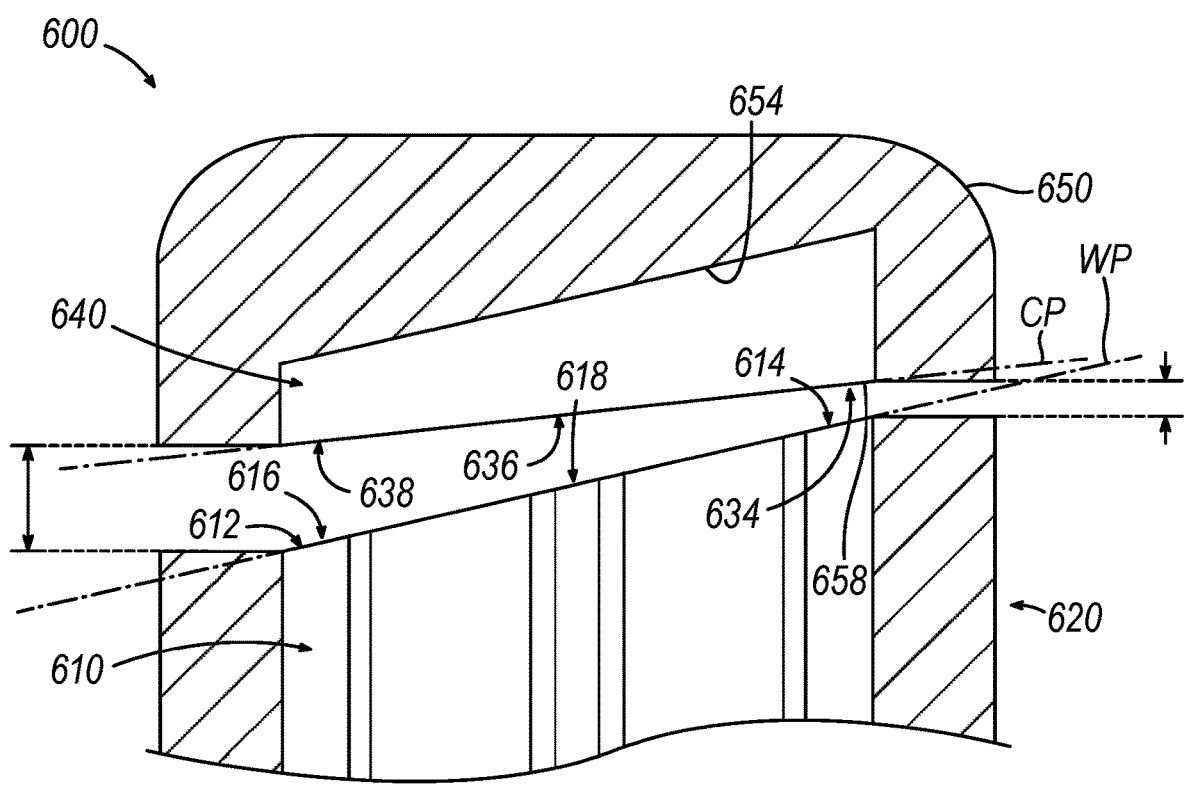
FIG. 10 depicts a cross-sectional side view of yet another exemplary end effector including a stapling head assembly and an anvil for use with the circular stapler of FIG. 1, with the anvil spaced apart from the stapling head assembly.

B. Second Exemplary Non-Circular End Effector Having Angled Knife Edge and Angled Washer In some instances, it may be desirable to substitute an angled knife member (610) and an angled washer (640) to promote a progressive slicing-type cutting action, rather than an abrupt guillotine-type cutting action, to minimize the force required to cut through tissue and angled washer (640). FIGS. 10-11C schematically show a portion of another example of a non-circular end effector (600) that operates in such a manner, where end effector (600) includes a stapling head assembly (620) having an angled knife member (610), and an anvil (650) having an angled washer (640). Non-circular end effector (600) is constructed and operable similar to end effector (500) described above, except as otherwise described below.

As shown in FIG. 10, knife member (610) includes a knife edge (612) defining a single cutting edge plane (CP) that intersects and is obliquely angled relative to central axis (CA). Knife edge (612) includes a first edge portion (614), a second edge portion (616), and a third edge portion (618), where edge portions (614, 616, 618) are coplanar within cutting edge plane (CP). First edge portion (614) is located on a first side of central axis (CA) and second edge portion (616) is located on a second side of central axis (CA) along cutting edge plane (CP), such that first and second edge portions (614, 616) are diametrically opposed from one another about central axis (CA). Third edge portion (618) is located between first and second edge portions (614, 616) along cutting edge plane (CP). First edge portion (614) extends distally farther than second edge portion (616). Third edge portion (618) is disposed between first edge portion (614) and second edge portion (616).

Anvil (650) differs from anvil (550) in that anvil (650) includes angled washer (640) having an angled proximal surface (658) with a distal first washer portion (634) on a first side of central axis (CA), a proximal second washer portion (636) on a second side of central axis (CA), and a third washer portion (638) therebetween through which central axis (CA) extends. Proximal surface (658) defines a washer plane (WP) that intersects central axis (CA) at an oblique angle such that washer plane (WP) is non-parallel relative to central axis (CA). In some versions, washer (640) may be non-angled such that proximal surface (658) is perpendicular relative to central axis (CA). In the present version, washer plane (WP) and cutting edge plane (CP) intersect central (CA) at different oblique angles, such that washer plane (WP) is angled relative to cutting edge plane (CP). In the present version, washer plane (WP) is less steeply angled than cutting plane (CP) relative to central axis (CA). However, both washer plane (WP) and cutting edge plane (CP) slope in the same direction such that the distal-most first edge portion (614) of knife member (610) is aligned with the distal-most first washer portion (634) of washer proximal surface (658), as shown in FIG. 10. In yet other versions, washer plane (WP) and cutting edge plane (CP) may be sloped in different directions, for example such that the distal-most first edge portion (614) of knife member (610) is aligned with the proximal-most second washer portion (638) of washer proximal surface (658).

Figure 11A:
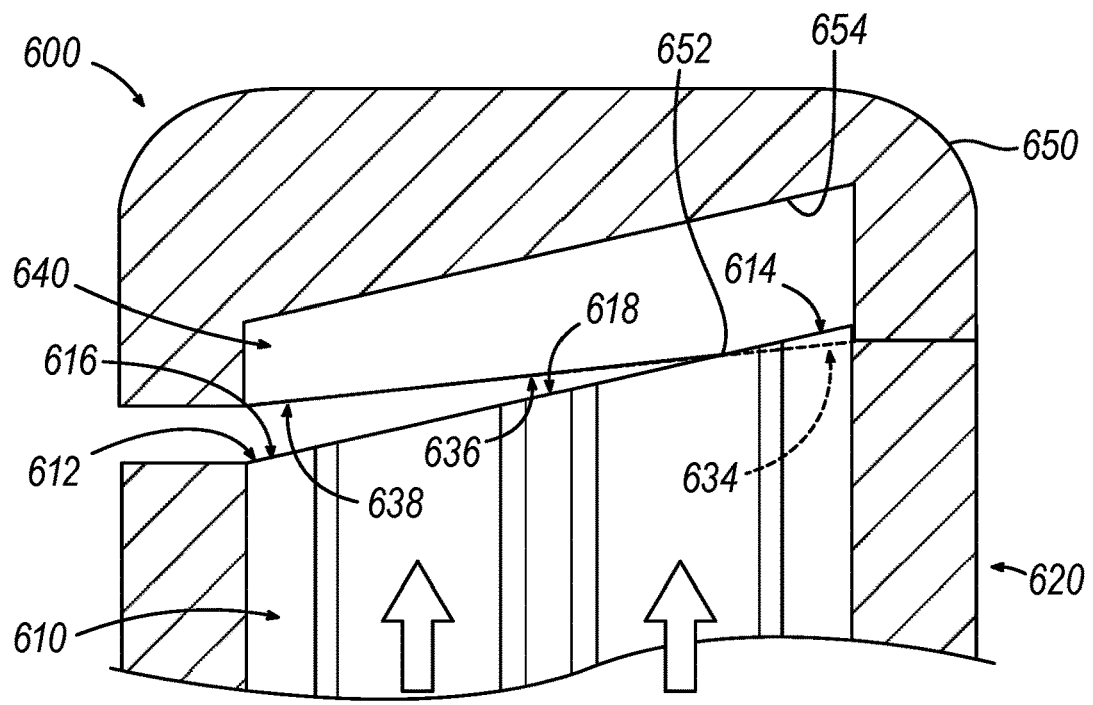
FIG. 11A depicts a cross-sectional side view of the stapling head assembly and the anvil of FIG. 10, with the knife member engaging a first side portion of a washer of the anvil on a first side of the central axis.

FIG. 11A schematically shows knife edge (612) being transitioned distally towards anvil (650). First edge portion (614) engages and cuts through first washer portion (634) at a distal advancing point of contact (652). Point of contact (652) is located where cutting edge plane (CP) distally intersects washer plane (WP) and a portion of knife edge (612) engages a portion of proximal surface (658). Knife edge (612) engages and cuts at point of contact (652) in a distal slicing manner through the tubular anatomical structures (20, 40) of a patient before cutting washer (640). While only one point of contact (652) is shown, it will be appreciated that the circumferentially closed configuration of knife edge (612) about central axis (CA) may yield two opposed points of contact (652) throughout the distal cutting stroke of knife member (610).

Figure 11B:
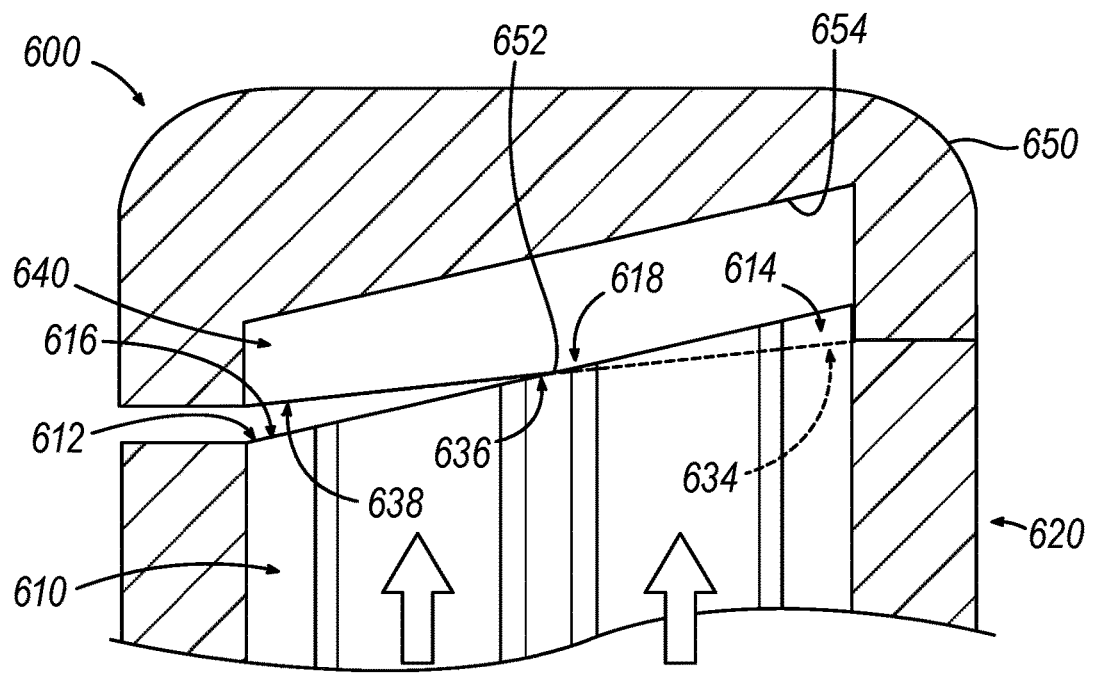
FIG. 11B depicts a cross-sectional side view of the stapling head assembly and the anvil of FIG. 10, with the knife member engaging a middle portion of the washer through which the central axis extends.
Figure 11C:
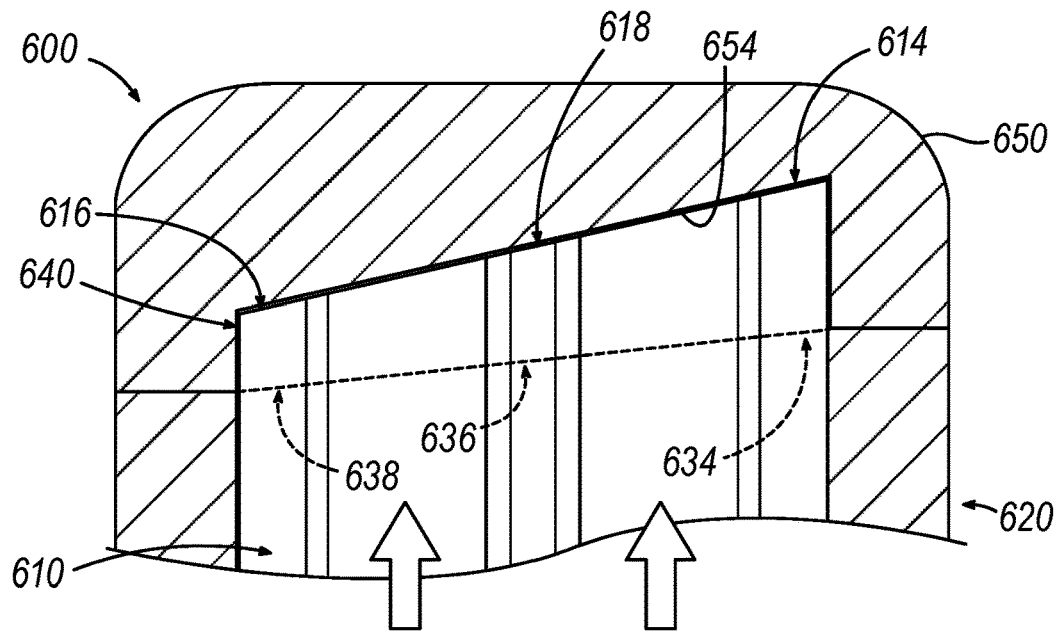
FIG. 11C depicts a cross-sectional side view of the stapling head assembly and the anvil of FIG. 10, with the knife member engaging a second side portion of the washer on a second side of the central axis.

FIG. 11B schematically shows knife edge (612) being transitioned further distally through third washer portion (638) after cutting through the tubular anatomical structures (20, 40) at point of contact (652) between third edge portion (618) and third washer portion (638). As knife edge (612) translates distally, point of contact (652) moves along washer plane (WP) from first washer portion (634) through third washer portion (638), as shown.

FIG. 11C schematically shows knife edge (612) fully transition distally through angled washer (640) and transect angled washer (640). Cutting edge plane (CP) has fully passed distally through washer plane (WP), and knife edge (612) may confront a washer seat (654). The completion of this slicing stroke may produce audible and/or tactile feedback to the user to indicate completion of tissue cutting and stapling.

Figure 12:
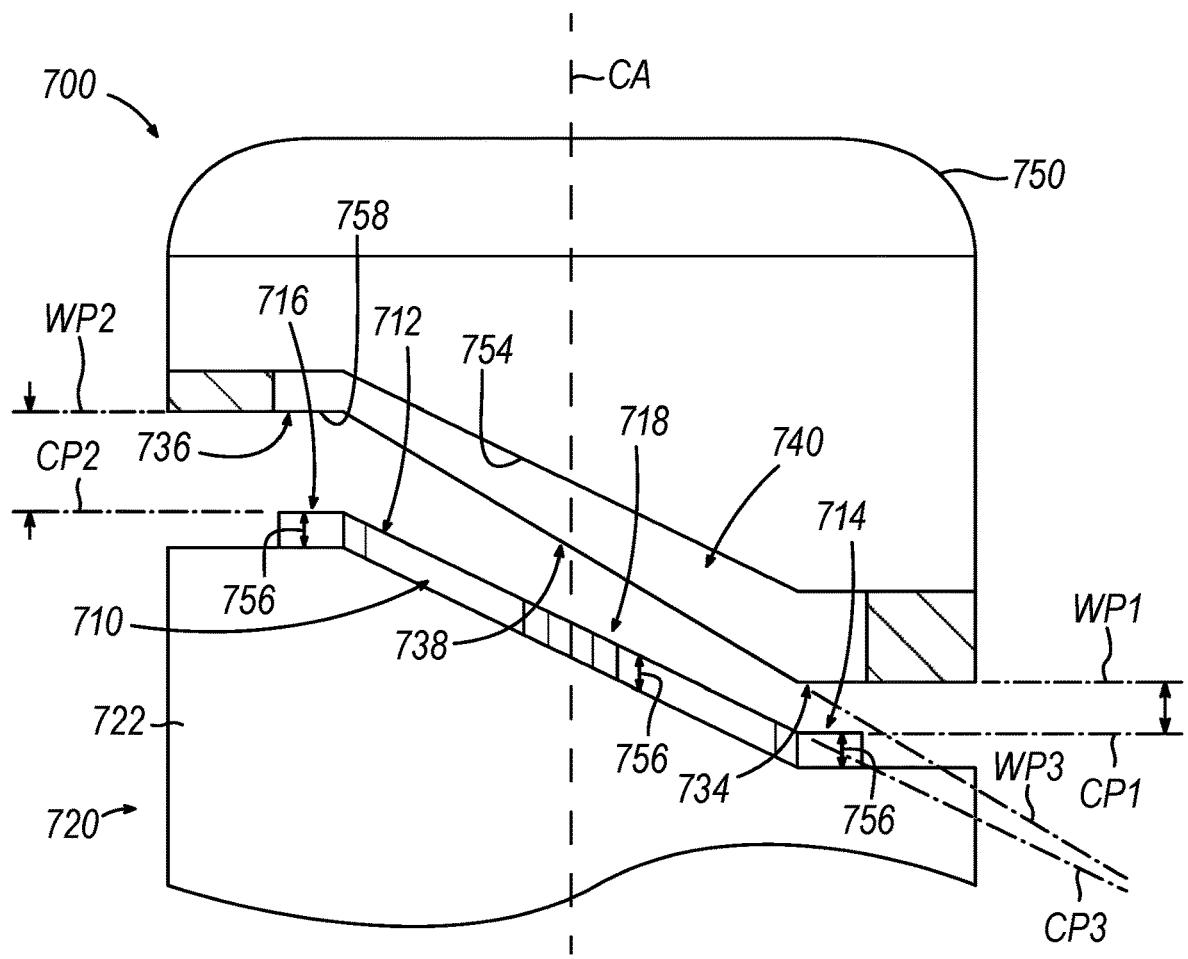
FIG. 12 depicts a cross-sectional side view of yet another exemplary stapling head assembly and anvil, with the anvil spaced apart from the stapling head assembly.

C. Third Exemplary Non-Circular End Effector Having Angled Knife Member with an Angularly Stepped Knife Edge and Angularly Stepped Washer In some instances, it may be desirable to substitute a knife member (710) including a stepped knife edge (712) and an anvil (750) including a stepped washer (740) to promote a slicing-type cutting action to minimize the force required to cut through tissue and stepped washer (740). FIGS. 12-13C schematically show a third example of a non-circular end effector (700) that operates in such a manner, where end effector (700) includes a stapling head assembly (720) having a knife member (710) with an angularly stepped knife edge (712), and an anvil (750) having an angularly stepped washer (740). Non-circular end effector (700) is constructed and operable similar to non-circular end effector (600) described above, except as otherwise described below.

As shown in FIG. 12, stepped knife edge (712) has a first edge portion (714) defining a first cutting edge plane (CP1) that intersects and is perpendicular relative to central axis (CA); a second edge portion (716) defining second cutting edge plane (CP2) that is also perpendicular relative to central axis (CA) and thus parallel to first cutting edge plane (CP1); and a third edge portion (719) defining a third cutting edge plane (CP3) that is obliquely angled relative to central axis (CA) and each of first cutting edge plane (CP1) and second cutting edge plane (CP2). First edge portion (714) is located on a first side of central axis (CA) and second edge portion (716) is located on a second side of central axis (CA) such that first and second edge portions (714, 716) are diametrically opposed from one another. Third edge portion (718) extends obliquely between first and second edge portions (714, 716) across central axis (CA). In other versions, first and second cutting planes (CP1, CP2) may be non-perpendicular to central axis (CA).

Anvil (750) differs from anvil (650) in that anvil (750) includes stepped washer (740) having a proximal surface (758) that defines more than one washer plane relative to central axis (CA). In particular, proximal surface (758) includes a first washer portion (734) defining a first washer plane (WP1) perpendicular to central axis (CA); a second washer portion (736) diametrically opposed from first washer portion (734) and defining a second washer plane (WP2) perpendicular to central axis (CA) and parallel to first washer plane (WP1); and a third washer portion (738) defining a third washer plane (WP3) obliquely angled relative to central axis (CA) and each of first washer plane (WP1) and second washer plane (WP2). Third washer plane (WP3) is angled more steeply than third cutting edge plane (CP3) angle relative to central axis (CA). Third washer plane (WP3) slopes in the same direction as third cutting edge plane (CP3) such that the distal-most second edge portion (716) of knife member (710) is aligned with the distal-most second washer portion (736) of washer (740). First washer portion (734) is more proximally located relative to second washer portion (736) and has a greater axial thickness than second washer portion (736). Accordingly, at any given longitudinal position of anvil (750) relative to stapling head assembly (720) prior to engagement between knife member (710) and washer (740), the axial gap between second edge portion (716) and second washer portion (736) is larger than the axial gap between first edge portion (714) and first washer portion (734). Third washer portion (738) has an axial thickness that varies in a radial direction between first washer portion (734) and second washer portion (736).

Figure 13A:
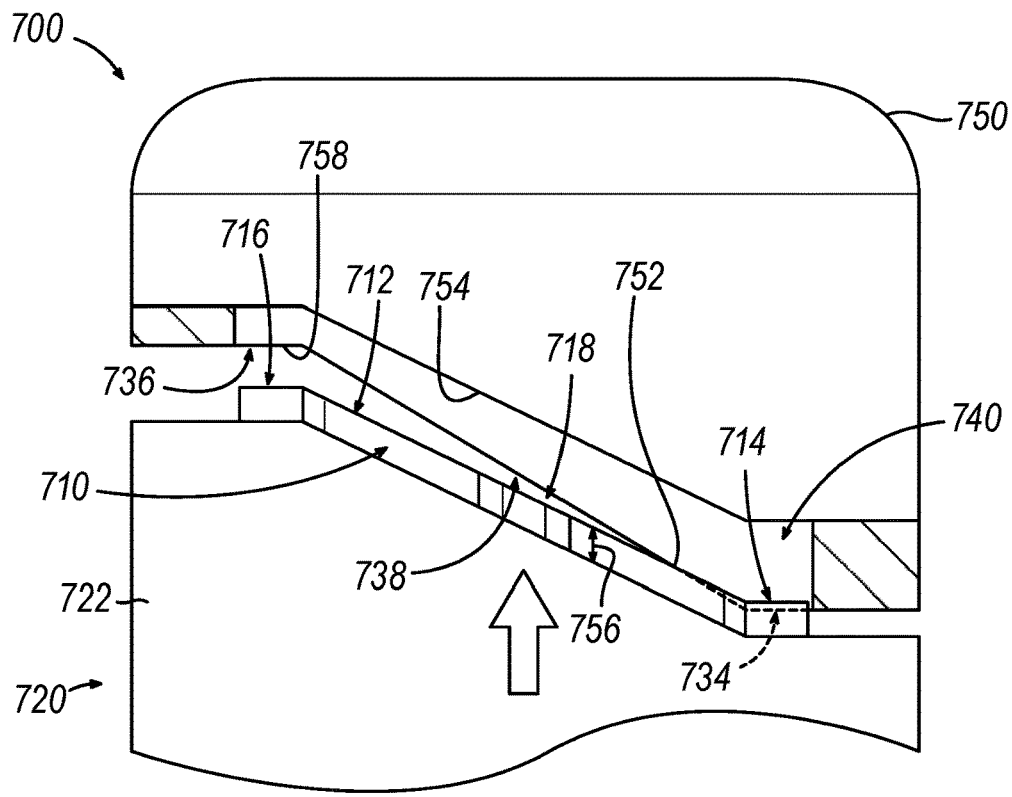
FIG. 13A depicts a cross-sectional side view of the stapling head assembly and anvil of FIG. 12, with the knife member engaging the washer on a first side portion on a first side of the central axis.

FIG. 13A schematically shows stepped knife edge (712) being transitioned distally towards stepped washer (740). First edge portion (714) has engaged and cut through first washer portion (734) after cutting through a corresponding portion of tubular anatomical structures (20, 40) disposed between first edge portion (714) and first washer portion (734), with a guillotine-type cutting action. The portions of tubular anatomical structures (20, 40) disposed between third edge portion (718) and third washer portion (738) are then progressively cut at a distally advancing point of contact (752) located at the intersection between third cutting edge plane (CP3) and third washer plane (WP3) with a slicing-type cutting action. This progressive slicing of third washer portion (738) and corresponding tissue by third edge portion (718) may require less force at any given position of point of contact (752) as compared to the force required to cut first washer portion (734) and corresponding tissue with first edge portion (714) and the force required to cut second washer portion (736) with second edge portion (716). In FIG. 13A, point of contact (752) is at an intersection of third cutting edge plane (CP3) and third washer plane (WP3). First edge portion (714) is distally passing first washer portion (734) and a portion of third edge portion (718) is partially passing a portion of third washer portion (738). In some versions, third edge portion (718) may begin to engage third washer portion (738) while first edge portion (714) engages first washer portion (734) or after first edge portion (714) has engaged entirety of first washer portion (734).

Figure 13B:
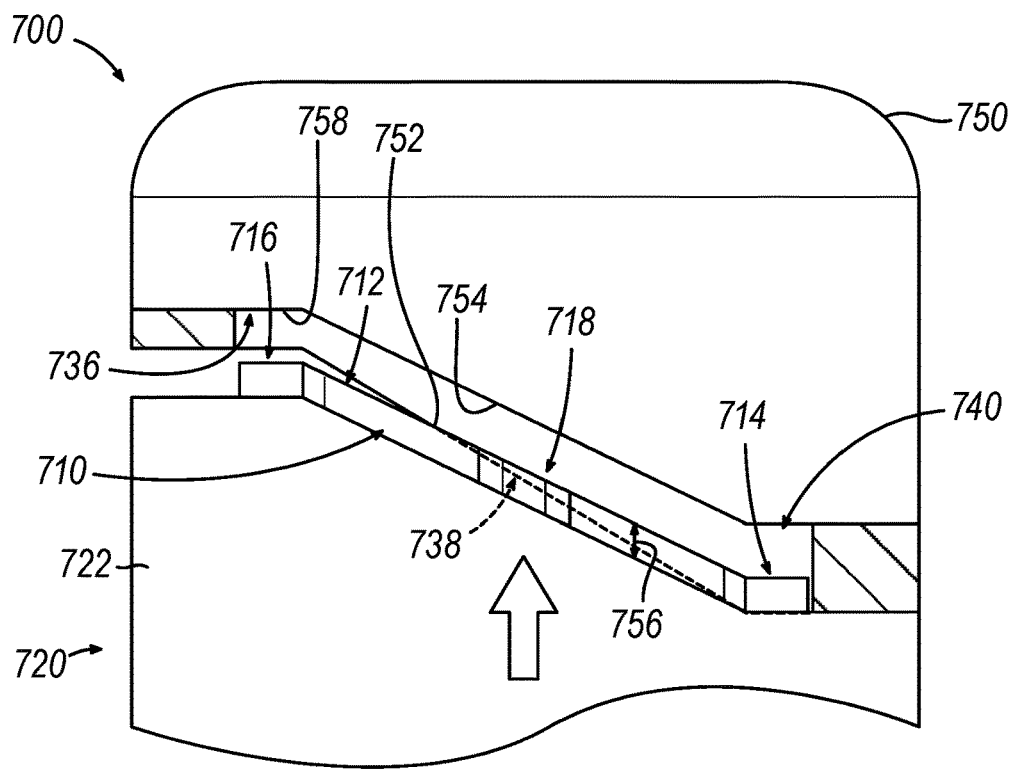
FIG. 13B depicts a cross-sectional side view of the stapling head assembly and anvil of FIG. 12, with the knife member engaging a middle portion of the washer through which the central axis extends.
Figure 13C:
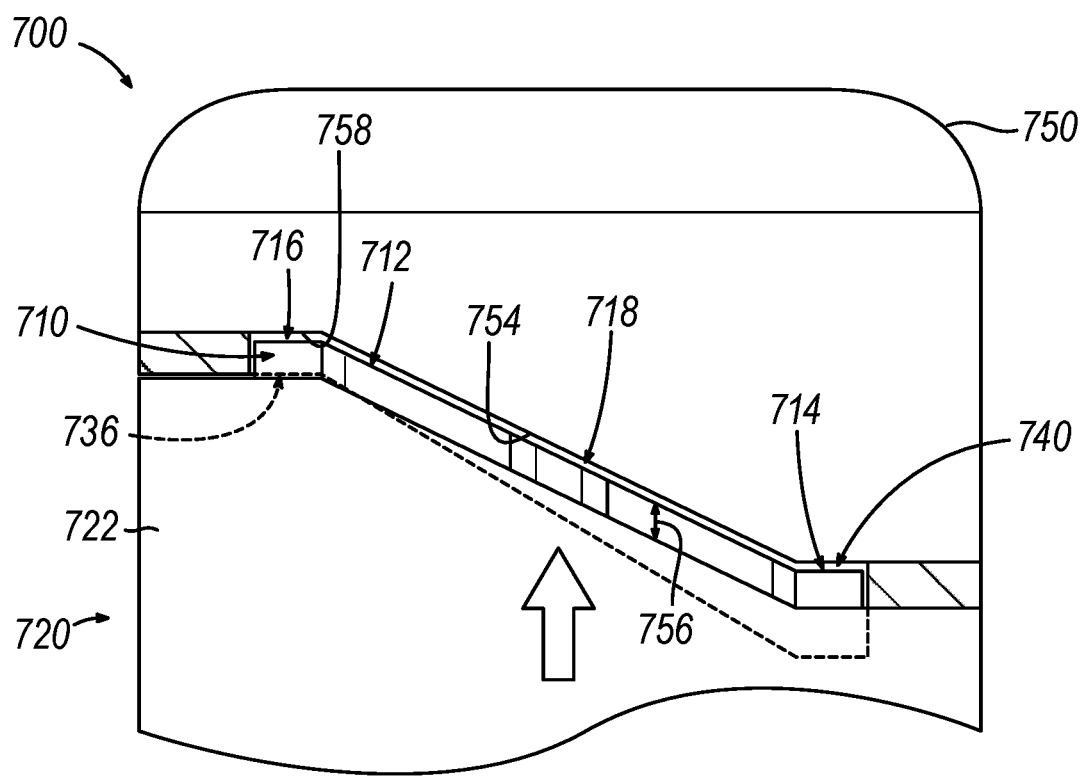
FIG. 13C depicts a cross-sectional side view of the stapling head assembly and anvil of FIG. 12, with the knife member engaging a second side portion of the washer on a second side of the central axis.

FIG. 13B schematically shows stepped knife edge (712) being transitioned further distally through third washer portion (738) and corresponding portions of tubular anatomical structures (20, 40) at point of contact (752) between third edge portion (718) and third washer portion (738) in a slicing manner. As stepped knife edge (712) translates distally, point of contact (752) moves distally along third washer plane (WP3) until third cutting edge plane (CP3) fully passes distally through all of third washer plane (WP3) at an intersection of third washer plane (WP3) and second washer plane (WP2).

FIG. 13C schematically shows stepped knife edge (712) fully transitioned distally and fully transecting stepped washer (740). Second edge portion (716) has cut through the second washer portion (736) and corresponding portions of tubular anatomical structures (20.40) in a guillotine manner all at once. Cutting edge planes (CP1, CP2, CP3) have fully passed distally through washer planes (WP1, WP2, WP3), and stepped knife edge (712) may confront a washer seat (754). The completion of this slicing stroke may produce audible and/or tactile feedback to the user to indicate completion of tissue cutting and stapling.

Figure 14:
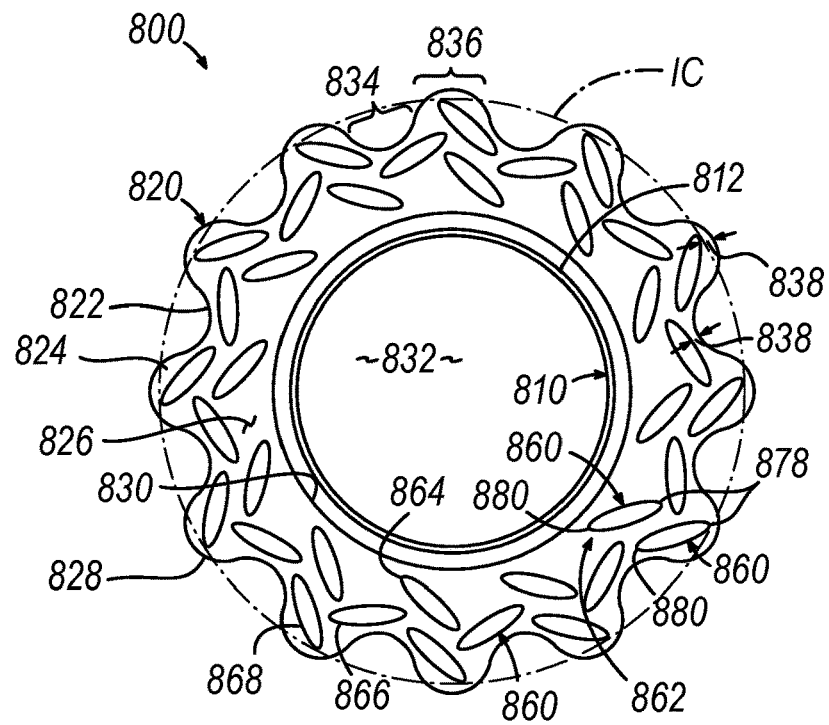
FIG. 14 depicts a top plan view of an exemplary stapling head assembly including a deck member with an undulating exterior perimeter and a circular interior perimeter, and a circular knife member.

D. Exemplary Stapling Head Assembly with an Undulating Exterior Perimeter and Circular Knife Member FIG. 14 shows a portion of another example of a stapling head assembly (820) for use with an instrument (10) configured to create an anastomosis defining a larger lumen between tubular anatomical structures (20,40) of a patient while minimizing the cross-sectional area of stapling head assembly (820). Stapling head assembly (820) may be constructed and operable similar to stapling head assembly (300), except as otherwise described below.

In this example, stapling head assembly (820) includes a body member (822) extending distally from shaft assembly (200) and a knife member (810) located within body member (822). Stapling head assembly (820) further includes a deck member (824) located within a distal end of body member (822). Deck member (824) has a distally presented stapling surface in the form of a deck surface (826). Deck surface (826) includes a non-circular, undulating (also referred to as sinuous) exterior perimeter (828) and a circular interior perimeter (830), and staple openings (860). Undulating exterior perimeter (828) includes concave portions (834) and convex portions (836). Concave and convex portions (834, 836) define an imaginary circumference (IC) farther spaced from central axis (CA) relative to spacing between circular interior perimeter (830) and central axis (CA). Imaginary circumference (IC) is a midline defined by alternating concave and convex portions (834, 836) of undulating exterior perimeter (828). Concave and convex portions (834, 836) are configured allow for a minimum distance (838) from staple openings (860) to undulating exterior perimeter (828). Minimum distance (838) allows adequate spacing for effective stapling while allowing the tubular anatomical structure (20,40) to conform to the undulating exterior perimeter (828) during insertion of end effector (800) within the body without over expanding the tubular anatomical structure (20,40). Circular interior perimeter (830) defines a circular lumen (832). Circular Knife member (810) includes a circular knife edge (812) concentrically located within circular lumen (832). Circular knife edge (812) is complements and conforms to circular interior perimeter (830).

Staple openings (860) are arranged in an array of staple openings (862) including a first row (864), a second row (866), and third row (868) of staple openings (860) concentrically arranged on deck surface (826) between undulating exterior and circular interior perimeters (828, 830). First row (864) is concentrically arranged within second row (866), and second row (866) is concentrically arranged within third row (868).

Staple openings (860) are oval shaped and include a first end (878) and a second end (880) and are angularly oriented relative to circular interior perimeter (830). First end (878) of first and third row (864, 868) are spaced a shorter radial distance from circular interior perimeter (830) relative to second end (880). Second end (880) of first and third row (864, 868) is spaced a father radial distance relative to circular interior perimeter (830).

Staple openings (860) of second row (866) are angularly arranged at an oppose angle relative to circular interior perimeter (830). First end (878) of staple opening (860) of second row (866) is spaced a farther radial distance from circular interior perimeter (830) relative to second end (880) of staple opening (860). Staple openings (860) located in second and third row (866, 868) further define undulating exterior perimeter (828). Staple openings (860) in third row (868) further defines convex portion (836) and staple openings (860) in second row (866) further defines concave portion (834) so that staple openings (860) are a minimum distance (838) from undulating exterior perimeter (828).

In summary, and as shown in FIG. 14, each staple opening (860) of deck member (824) extends angularly and nontangentially relative to imaginary circumference (IC). Accordingly, staples deployed distally through staple openings (860) and into tissue are configured to define an array of formed staples that is expandable radially outwardly to accommodate radial expansion and similar movements of the stapled tissue at the anastomosis. The undulating shape of exterior perimeter (828) of deck member (824) provides deck surface (826) with sufficient surface area to accommodate three annular rows of angled staple openings (860) such that any given imaginary radial line drawn outwardly from a central axis of deck member (824) extends through at least one staple opening (860), thus ensuring proper sealing of the tissue with staples. Furthermore, the undulating shape of exterior perimeter (828) of deck member (824) minimizes the resultant outer diameter of stapling head assembly (820), thus enabling the corresponding surgical instrument to be manipulated and positioned more easily via minimal contact with the inner walls of tubular anatomical structures (20, 40). Finally, though not shown, it will be appreciated that an exterior perimeter of the corresponding anvil may be formed with a similar undulating shape.

Figure 15:
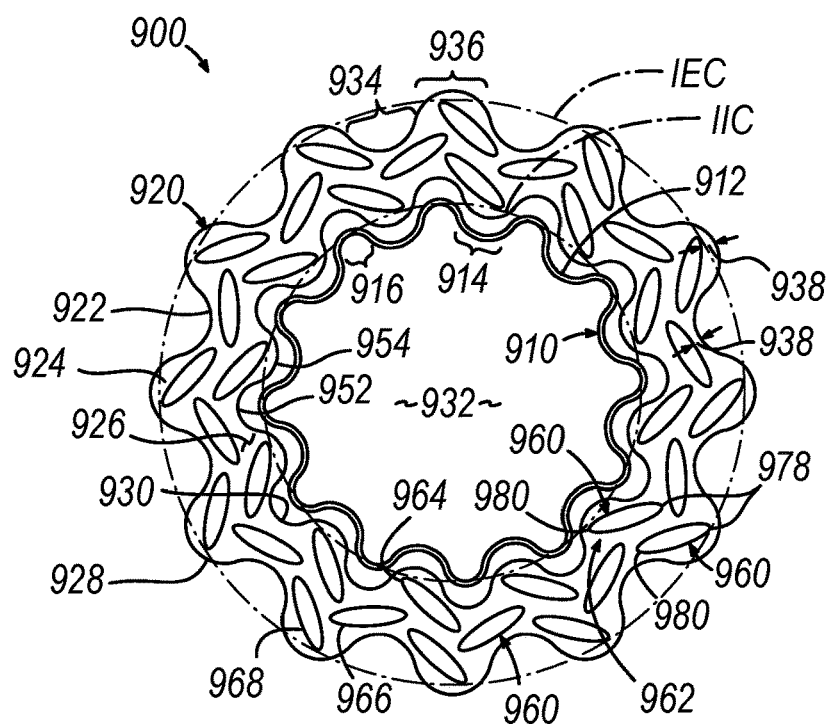
FIG. 15 depicts a top plan view of an exemplary stapling head assembly including a deck member with an undulating exterior perimeter and an undulating interior perimeter, and an undulating knife member.

E. Exemplary Non-Circular Stapling Head Assembly with Undulating Perimeters and Undulating Knife Member FIG. 15 shows a portion of another example of a non-circular stapling head assembly (920) for use with instrument (10). Non-circular stapling head assembly (920) is configured to create an anastomosis defining a larger lumen between tubular anatomical structures (20, 40) of a patient while minimizing the cross-sectional area of the non-circular stapling head assembly (920). Non-circular stapling head assembly (920) is constructed and operable similar to stapling head assembly (820), except as otherwise described below.

In this example, non-circular stapling head assembly (920) includes a body member (922) extending distally from shaft assembly (200) and an undulating knife member (1010) located within body member (922). Stapling head assembly (920) further includes a deck member (924) located within a distal end of body member (922). Deck member (924) includes a distally presented stapling surface in the form of a deck surface (926). Deck surface (926) includes a non-circular, undulating exterior perimeter (928); a non-circular, undulating interior perimeter (930); and staple openings (960). Exterior and interior undulating perimeters (928, 930) define imaginary exterior and interior circumferences (IEC, IIC) spaced from central axis (CA). Imaginary exterior circumference (IEC) is spaced a further distance than imaginary interior circumference (IIC). Exterior and interior imaginary circumferences (IEC, IIC) are midlines for respective exterior concave and convex portions (934, 936) and interior concave and convex portions (952, 954). Exterior concave and convex portions (934, 936) and interior concave and convex portions (952, 954) are configured allow for a minimum distance (938) from staple openings (960) to undulating exterior perimeter (928). Minimum distance (938) allows adequate spacing for effective stapling while allowing the tubular anatomical structure (20, 40) to conform to undulating exterior perimeter (928) during insertion without overly expanding the tubular anatomical structure (20, 40).

Interior concave and convex portions (952, 954) are circumferentially clocked a few degrees from exterior convex and concave portions (936, 934), respectively. In some versions, interior concave and convex portions (952, 954) are circumferentially aligned with exterior convex and concave portions (936, 934), respectively. Interior concave and convex portions (952, 954) are spaced a minimum distance (938) from staple openings (960). Minimum distance (938) allows for effective stapling, while providing creation of a larger lumen within the tubular anatomical structure (20, 40). Undulating interior perimeter (930) defines an undulating lumen (932). Undulating knife member (910) includes an undulating knife edge (912) concentrically located within undulating lumen (932). Undulating knife edge (912) complements the shape of interior concave and convex portions (952, 954) of undulating interior perimeter (930). Undulating knife edge (912) includes concave and convex edge portions (914, 916) that complement respective interior convex and concave portions (954, 952).

Staple openings (960) are arranged in an array of staple openings (962) including a first, second, and third row of staple openings (964, 966, 988) concentrically arranged on deck surface (926) between undulating exterior and interior perimeters (928, 930). First row (964) is concentrically arranged within second row (966), and second row (966) is concentrically arranged within third row (986). Staple openings (960) are oval shaped and include a first end (978) and a second end (980). Each of staple openings are angularly oriented relative to central axis (CA). First ends (978) of staple openings (960) of first and third row (964, 968) are spaced a shorter radial distance from central axis (CA) relative to second end (980). Staple openings (960) of second row (966) are arranged with an opposite angle relative to angle of staple openings (960) of first and third row (964, 966). First ends (978) of second row (966) are spaced a farther radial distance from central axis (CA) relative to second end (980).

The undulating shape of exterior perimeter (928) of deck member (924) maximizes the resultant outer diameter of deck member (924) and stapling head assembly (920), thus enabling the corresponding surgical instrument to be manipulated and positioned more easily via minimal contact with the inner walls of tubular anatomical structures (20, 40). Additionally, the undulating shape of interior perimeter (930) of deck member (924) maximizes the resultant inner diameter of deck member (924) and thus the resultant outer diameter of the undulating shaped knife member (910), which allows for cutting tissue to create an anastomosis of an enlarged resultant diameter having the benefits described above.

Figure 16:
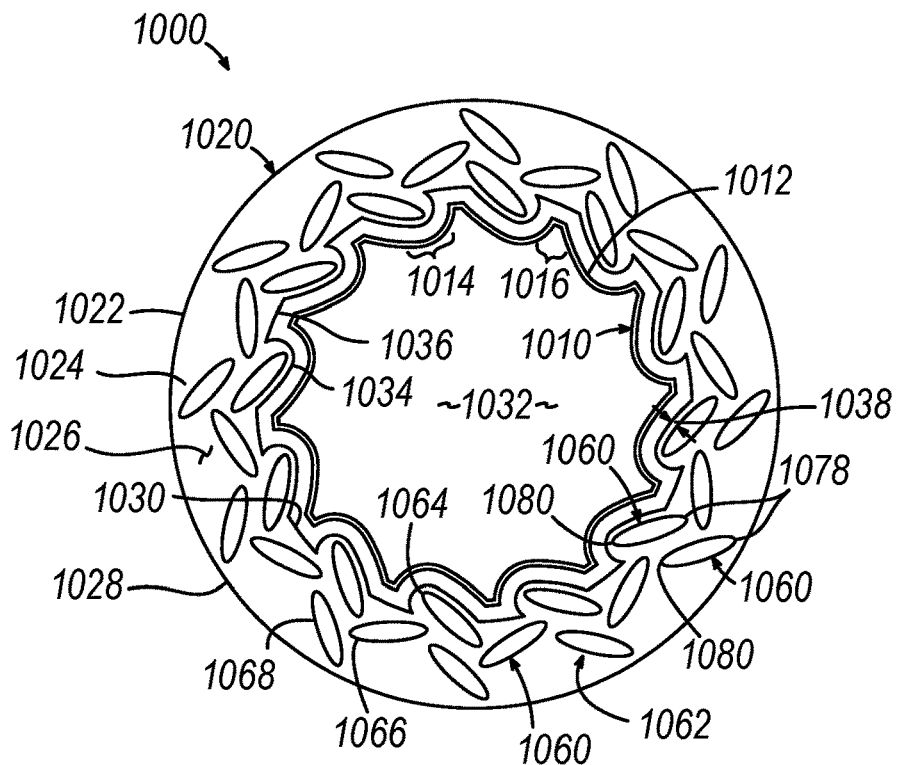
FIG. 16 depicts a top plan view of an exemplary stapling head assembly including a deck member with a circular exterior perimeter and a sawblade shaped interior perimeter, and a sawblade shaped knife member.

F. Exemplary Stapling Head Assembly with Circular Exterior Perimeter and Sawblade Knife Member FIG. 16 shows a portion of another example of a stapling head assembly (1020) suitable for use with instrument (10) and configured to create an anastomosis defining a larger lumen between tubular anatomical structures (20, 40) of a patient. Stapling head assembly (1020) is constructed and operable similar to stapling head assemblies (820, 920), except as otherwise described below.

In this example, stapling head assembly (1020) includes a circular body member (1022) extending distally from shaft assembly (200) and an undulating knife member (1010) positioned within circular body member (1022). Stapling head assembly (1020) further includes a deck member (1024) located within a distal end of circular body member (1022). Deck member (1024) includes a distally presented stapling surface in the form of a deck surface (1026). Deck surface (1026) includes a circular exterior perimeter (1028);

a non-circular, sawblade shaped, interior perimeter (1030), and staple openings (1060) arranged in an array similar to the array of staple openings (862) of stapling head assembly (820).

Interior perimeter (1030) of deck member (1024) includes outwardly recessed tangent portions (1034) and inwardly protruding convex portions (1036). Tangent portions (1034) lie along an imaginary circumference (not shown). Tangent portions (1034) are connected to adjacent convex portions (1036) that curve inwards towards a central axis (not shown) and back to the imaginary circumference to next adjacent tangent portion (1034) along the imaginary circumference. Convex portions (1036) curve around staple openings (1060) with a minimum distance (1038) between convex portion (1036) and staple openings (1060). Minimum distance (1038) allows adequate spacing for effective stapling and allows sawblade-shaped knife member (1010) to have a larger resultant radius. Sawblade interior perimeter (1030) defines a sawblade shaped lumen (1032). Knife member (1010) is disposed within sawblade shaped lumen (1032) and includes a knife edge (1012) having tangent and convex portions (1034, 1036) giving knife edge (1012) a sawblade shape. Knife edge (1012) includes tangent and concave edge portions (1014, 1016) that complement tangent and convex portions (1034, 1036) of interior perimeter (1030) of deck member (1024).

Figure 17:
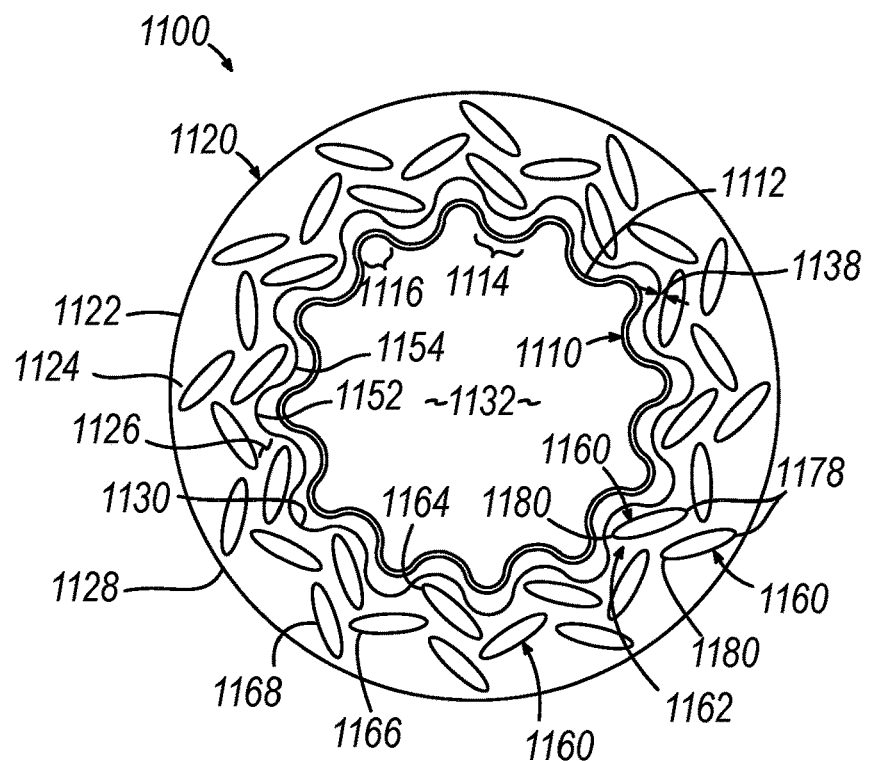
FIG. 17 depicts a top plan view of a stapling head assembly including a deck member with a circular exterior perimeter and an undulating interior perimeter, and an undulating knife member.

G. Exemplary Stapling Head Assembly with Circular Exterior Perimeter and Undulating Knife Member FIG. 17 shows a portion of another example of a stapling head assembly (1120) for use with instrument (10) configured to create an anastomosis defining a larger lumen between tubular anatomical structures (20, 40) of a patient. Stapling head assembly (1120) is constructed and operable similar to stapling head assemblies (820, 920, 1020), except as otherwise described below.

In this example, stapling head assembly (1120) includes a circular body member (1122) extending distally from shaft assembly (200) and an undulating knife member (1110). Stapling head assembly (1120) further includes a deck member (1124) disposed within body member (1122). Deck member (1124) includes a distally presented stapling surface in the form of a deck surface (1126). Deck surface (1126) includes a circular exterior perimeter (1128), a non-circular, undulating interior perimeter (1130), and an array of staple openings (1162) similar to the array of staple openings (1162) of stapling head assembly (1020). Undulating interior perimeter (1130) includes alternating concave and convex portions (1152, 1154). Undulating interior perimeter (1130) defines an imaginary circumference (not shown) that is a midline between concave and convex portions (1152, 1154). Concave and convex portions (1152, 1154) are configured to allow for a minimum distance (1138) between staple openings (1160) and undulating interior perimeter (1130). Minimum distance (1138) allows adequate spacing for effective stapling and allowing undulating knife member (1010) to have a larger resultant radius. Undulating knife member (1110) includes an undulating knife edge (1112) having alternating concave and convex edge portions (1114, 1116) that complement convex and concave portions (1154, 1152), respectively, of deck member (1124).

III. Exemplary Combinations

The following examples relate to various non-exhaustive ways in which the teachings herein may be combined or applied. The following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument comprising: (a) a stapling assembly including: (i) a housing extending distally along a central axis, (ii) a deck member having a plurality of staple openings configured to receive a plurality of staples, wherein the deck member includes an exterior perimeter having a first shape and an interior perimeter enclosed by the exterior perimeter and having a second shape different than the first shape, and (iii) a knife member at least partially disposed within the housing, wherein a distal end of the knife member includes a cutting edge defining an edge plane that intersects the central axis, wherein the cutting edge has a non-circular shape in the edge plane; and (b) an anvil configured to selectively couple with the stapling assembly to compress tissue and form staples in the tissue.

Example 2

The surgical instrument of Example 1, wherein the cutting edge includes at least one first edge portion and at least one second edge portion, wherein the first edge portion has a first length and the second edge portion has a second length, wherein the first length is greater than the second length.

Example 3

The surgical instrument of Example 2, wherein the first length is greater than the second length by a ratio of 3:1.

Example 4

The surgical instrument of any of Examples 2 through 3, wherein the first edge portion is linear, and the second edge portion is arcuate.

Example 5

The surgical instrument of any of the preceding Examples, wherein the non-circular shape of the cutting edge is complementary to the second shape of the interior perimeter of the deck member.

Example 6

The surgical instrument of any of the Examples 2 through 5, wherein the deck member includes a first array of staple openings proximate to the first edge portion and a second array of staple openings proximate to the second edge portion, wherein the first array of staple openings is different than the second array of staple openings.

Example 7

The surgical instrument of any of the preceding Examples, wherein the edge plane is orthogonal to the central axis.

Example 8

The surgical instrument of any of the Examples 2 through 7, wherein the at least one first edge portion comprises a pair of first edge portions and the at least one second edge portion comprises a pair of second edge portions, wherein the first edge portions are opposed from one another about the central axis and the second edge portions are opposed from one another about the central axis, wherein the first edge portions are interconnected by the second edge portions.

Example 9

The surgical instrument of Examples 8, wherein the stapling assembly further includes a coupling feature configured to couple with the anvil, wherein each of the first edge portions includes a radially outwardly protruding central portion shaped to accommodate the coupling feature.

Example 10

The surgical instrument of any of the preceding Examples, wherein the cutting edge has a dog bone shape in the edge plane.

Example 11

The surgical instrument of any of the preceding Examples, wherein the cutting edge has a flower shape in the edge plane.

Example 12

The surgical instrument of any of the preceding Examples, wherein the cutting edge has a sinuous shape in the edge plane.

Example 13

The surgical instrument of any of the preceding Examples, wherein the cutting edge includes a tangential portion and a sinuous portion.

Example 14

The surgical instrument of any of the preceding Examples, wherein the exterior perimeter of the deck member has a sinuous shape in a plane that intersects the central axis.

Example 15

The surgical instrument of any of the Examples 1 through 13, wherein the exterior perimeter of the deck member has an oval or circular shape in a plane that intersects the central axis.

Example 16

A surgical instrument comprising: (a) a stapling assembly including: (i) a housing extending distally along a central axis, (ii) a deck surface having an annular array of staple openings configured to receive a plurality of staples, and (iii) a knife member at least partially disposed within the housing, wherein a distal end of the knife member includes a cutting edge having a first edge portion and a second edge portion that are diametrically opposed about the central axis, wherein the first edge portion extends distally farther than the second edge portion; and (b) an anvil configured to releasably couple and cooperate with the stapling assembly to compress, staple, and cut tissue positioned therebetween, wherein the anvil includes a washer configured to be cut by the knife member after the knife member cuts the tissue.

Example 17

The surgical instrument of Example 16, wherein the cutting edge includes an edge portion defining a cutting edge plane that is obliquely angled relative to the central axis.

Example 18

The surgical instrument of any of Examples 16 through 17, wherein the washer includes a washer portion defining a washer plane that intersects the central axis and is non-parallel relative to the cutting edge plane.

Example 19

The surgical instrument of any of Examples 16 through 18, wherein the cutting edge includes a second edge portion that defines a second cutting edge plane that is non-parallel relative to the cutting edge plane.

Example 20

A surgical instrument comprising: (a) a stapling assembly including: (i) a housing extending distally along a central axis, (ii) a deck surface including an annular array of staple openings configured to receive a plurality of staples, an exterior perimeter, and an interior perimeter enclosed by the exterior perimeter, wherein the exterior perimeter has a first shape and the interior perimeter has a second shape different than the first shape, and (iii) a knife member disposed within the interior perimeter of the deck surface, wherein a distal end of the knife member includes a cutting edge having an edge shape in a plane that intersects the central axis, wherein the edge shape is complementary to the second shape; and (b) an anvil configured to releasably couple and cooperate with the stapling assembly to compress, staple, and cut tissue positioned therebetween.

Example 21

The surgical instrument of Example 20, wherein the second shape includes an alternating pattern about the central axis.

Example 22

A method of using a surgical instrument, the surgical instrument comprising a stapling assembly extending along a central axis and including an annular array of staples and a knife member, and an anvil configured to releasably couple with the stapling assembly and including a washer, the method comprising: (a) advancing the knife member towards the washer; (b) cutting through a first portion of the washer with the knife member, wherein the first portion is disposed on a first radial side of the central axis; and (c) after cutting through at least a portion of the first portion, cutting through a second portion of the washer with the knife member, wherein the second portion is disposed on a second radial side of the longitudinal axis.

IV. Miscellaneous

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Additionally, any one or more of the teachings herein may be combined with any one or more of the teachings of U.S. patent application Ser. No. 17/401,391, entitled "Methods of Forming an Anastomosis Between Organs with an Expandable Staple Pattern," filed on Aug. 13, 2023, published as U.S. Pub. No. 2023/0051305 on Feb. 16, 2023; U.S. patent application Ser. No. 17/401,428, entitled "Staple Forming Features for Circular Surgical Stapler," filed on Aug. 13, 2023 published as U.S. Pub. No. 2023/0047471 on Feb. 16, 2023; U.S. patent application Ser. No. 17/401,439, entitled "Circular Surgical Stapler End Effector Having Staple Line Alignment Feature," filed on Aug. 13, 2023, published as U.S. Pub. No. 2023/0049352 on Feb. 16, 2023; U.S. Pat. Applications. Ser. No. 17/401,444, entitled "Circular Surgical Stapler for Forming Pattern of Non-Tangential Staples," filed on Aug. 13, 2023, issued as U.S. Pat. No. 11,653,926 on May 23, 2023; U.S. patent application Ser. No. 17/401,451, entitled "Circular Surgical Stapler Having Staples with Expandable Crowns," filed on Aug. 13, 2023, published as U.S. Pub. No. 2023/0051659 on Feb. 16, 2023; and U.S. patent application Ser. No. 17/401,460, entitled "Circular Surgical Stapler for Forming Cross-Pattern of Staples," filed on Aug. 13, 2023, issued as U.S. Pat. No. 11,666,339 on Jun. 6, 2023. The disclosure of each of these US patent documents is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, California.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument comprising:
(a) a stapling assembly including:
  (i) a housing extending distally along a central axis,
  (ii) a deck member having a plurality of staple openings configured to receive a plurality of staples, wherein the deck member includes an exterior perimeter having a first elongate shape and an interior perimeter enclosed by the exterior perimeter and having a second elongate shape different than the first elongate shape, wherein the first elongate shape includes a pair of arcuate end portion and defines a longitudinal axis that extends through the arcuate end portions and intersects the central axis, and
  (iii) a knife member at least partially disposed within the housing, wherein a distal end of the knife member includes a cutting edge defining an edge plane that intersects the central axis, wherein the cutting edge has a non-circular shape in the edge plane; and
(b) an anvil configured to selectively couple with the stapling assembly to compress tissue and form staples in the tissue.

2. The surgical instrument of claim 1, wherein the cutting edge includes at least one first edge portion and at least one second edge portion, wherein the first edge portion has a first length and the second edge portion has a second length, wherein the first length is greater than the second length.

3. The surgical instrument of claim 2, wherein the first length is greater than the second length by a ratio of 3:1.

4. The surgical instrument of claim 2, wherein the first edge portion is linear and the second edge portion is arcuate.

5. The surgical instrument of claim 2, wherein the deck member includes a first array of staple openings proximate to the first edge portion and a second array of staple openings proximate to the second edge portion, wherein the first array of staple openings is different than the second array of staple openings.

6. The surgical instrument of claim 2, wherein the at least one first edge portion comprises a pair of first edge portions and the at least one second edge portion comprises a pair of second edge portions, wherein the first edge portions are opposed from one another about the central axis and the second edge portions are opposed from one another about the central axis, wherein the first edge portions are interconnected by the second edge portions.

7. The surgical instrument of claim 6, wherein the stapling assembly further includes a coupling feature configured to couple with the anvil, wherein each of the first edge portions includes a radially outwardly protruding central portion shaped to accommodate the coupling feature.

8. The surgical instrument of claim 1, wherein the non-circular shape of the cutting edge is complementary to the second elongate shape of the interior perimeter of the deck member.

9. The surgical instrument of claim 1, wherein the edge plane is orthogonal to the central axis.

10. The surgical instrument of claim 1, wherein the cutting edge has a dog bone shape in the edge plane.

11. The surgical instrument of claim 1, wherein the first elongate shape of the exterior perimeter further includes a pair of linear portions that interconnect the arcuate end portions, wherein the first elongate shape is positioned in a plane that intersects the central axis.

12. A surgical instrument comprising:
(a) a stapling assembly including:
    (i) a housing extending distally along a central axis,
    (ii) a deck surface including an annular array of staple openings configured to receive a plurality of staples, and
    (iii) a knife member at least partially disposed within the housing, wherein a distal end of the knife member includes a cutting edge having a first edge portion and a second edge portion that are diametrically opposed about the central axis, wherein the first edge portion extends distally farther than the second edge portion, wherein the cutting edge defines a cutting edge plane that is obliquely angled relative to the central axis, wherein an entirety of the cutting edge resides within the cutting edge plane; and
(b) an anvil configured to releasably couple and cooperate with the stapling assembly to compress, staple, and cut tissue positioned therebetween, wherein the anvil includes a washer configured to be cut by the knife member after the knife member cuts the tissue,
wherein the washer defines a washer plane that intersects the central axis and is non-parallel to the cutting edge plane such that the cutting edge is configured to engage the washer on a first side of the central axis before the cutting edge engages the washer on a second side of the central axis.

13. A surgical instrument comprising:
(a) a stapling assembly including:
    (i) a housing extending distally along a central axis,
    (ii) a deck member having a plurality of staple openings configured to receive a plurality of staples, wherein the deck member includes an exterior perimeter having a first elongate shape and an interior perimeter enclosed by the exterior perimeter and having a second elongate shape different than the first elongate shape, wherein the second elongate shape includes a pair of opposed elongate sides, wherein each of the opposed elongate sides includes a linear side portion and a radially outwardly recessed side portion, and
    (iii) a knife member at least partially disposed within the housing, wherein a distal end of the knife member includes a cutting edge defining an edge plane that intersects the central axis, wherein the cutting edge has a non-circular shape in the edge plane; and
(b) an anvil configured to selectively couple with the stapling assembly to compress tissue and form staples in the tissue.

14. The surgical instrument of claim 13, wherein the deck member includes a pair of end portions diametrically opposed from one another about the central axis, a pair of medial portions opposed from one another about the central axis, and a pair of central portions diametrically opposed from one another about the central axis, wherein the pair of end portions, the pair of medial portions, and the pair of central portions each have a different shape.

15. The surgical instrument of claim 14, wherein each of the central portions is located immediately adjacent to the central axis, wherein the pair of medial portions extend away from the pair of central portions to the pair of end portions, wherein each of the pair of end portions include an arcuate shape, wherein each of the end portions are positioned about a respective end axis.

16. The surgical instrument of claim 15, wherein each radially outwardly recessed side portions is defined by each of the central portions.

17. The surgical instrument of claim 13, wherein the linear side portion includes a first linear portion and the radially outwardly recessed side portion includes a second linear portion, wherein the first linear portion is parallel to the second linear portion.

* * * * *